(12) United States Patent
Peters et al.

(10) Patent No.: US 7,968,524 B2
(45) Date of Patent: Jun. 28, 2011

(54) METHODS OF ENHANCING LONG TERM MEMORY FORMATION BY INHIBITION OF GPR12

(75) Inventors: Marco Peters, La Jolla, CA (US); Roderick Euan Milne Scott, Poway, CA (US); Timothy P. Tully, Solana Beach, CA (US)

(73) Assignee: Helicon Therapeutics, Inc., San Diego, CA (US)

( * ) Notice: Subject to any disclaimer, the term of this patent is extended or adjusted under 35 U.S.C. 154(b) by 263 days.

(21) Appl. No.: 12/121,731

(22) Filed: May 15, 2008

(65) Prior Publication Data

US 2009/0022667 A1   Jan. 22, 2009

Related U.S. Application Data

(60) Provisional application No. 60/938,163, filed on May 15, 2007.

(51) Int. Cl.
A61K 31/70 (2006.01)
C07H 21/04 (2006.01)

(52) U.S. Cl. .......................... 514/44; 536/24.5

(58) Field of Classification Search .................. None
See application file for complete search history.

(56) References Cited

U.S. PATENT DOCUMENTS

| | | | |
|---|---|---|---|
| 5,684,143 A | 11/1997 | Gryaznov et al. | |
| 5,705,188 A | 1/1998 | Junichi et al. | |
| 5,858,988 A | 1/1999 | Wang | |
| 5,877,399 A * | 3/1999 | Hsiao et al. | 800/3 |
| 6,180,613 B1 | 1/2001 | Kaplitt et al. | |
| 6,291,438 B1 | 9/2001 | Wang | |
| 6,586,524 B2 | 7/2003 | Sagara | |
| 7,429,459 B2 * | 9/2008 | Merchiers et al. | 435/7.1 |
| 2004/0147429 A1 * | 7/2004 | Behan et al. | 514/2 |
| 2004/0203145 A1 | 10/2004 | Zamore et al. | |
| 2004/0220132 A1 * | 11/2004 | Kaemmerer | 514/44 |
| 2004/0224316 A1 * | 11/2004 | Tully et al. | 435/6 |
| 2004/0259247 A1 * | 12/2004 | Tuschl et al. | 435/375 |
| 2005/0266502 A1 | 12/2005 | Merchiers et al. | |
| 2006/0242724 A1 * | 10/2006 | Carlton et al. | 800/18 |
| 2006/0247194 A1 | 11/2006 | Mcswiggen et al. | |
| 2006/0247252 A1 | 11/2006 | Tully et al. | |
| 2007/0104688 A1 | 5/2007 | Rossi et al. | |

FOREIGN PATENT DOCUMENTS

| | | |
|---|---|---|
| WO | 2004013280 | 12/2004 |
| WO | 2005027628 | 3/2005 |

OTHER PUBLICATIONS

Hamann et al. (2002) Neuropsychologia 40:1187-1195.*
Abel et al., Cell 88:615-626 (1997).
Allshire, Science, 297, 1818-1819 (2002).
Bannai et al., Brain Res. Protoc., 3(1), 83 (1998).
Bettinger et al., Bioconjugate Chem., 10, 558-561 (1999).
Bourtchuladze et al., Cell 79, 59-68 (1994).
Bourtchuladze et al., Learn Mem. 5:365-374 (1998).
Broaddus et al., J. Neurosurg., 88(4), 734 (1998).
Choi et al., Bull. Korean Chem. Soc., 22, 46-52 (2001).
Diebold et al., Journal of Biological Chemistry, 274, 19087-19094 (1999).
Elbashir et al., Genes Dev., 15, 188 (2001).
Epa et al., Antisense Nuc. Acid Drug Dev., 10, 469 (2000).
Erbacher et al., Journal of Gene Medicine Preprint, 1, 1-18 (1999).
Fanselow et al., J Comp Physiol Psychol 93, 736-744 (1979).
Furgeson et al., Bioconjugate Chem., 14, 840-847 (2003).
Godbey et al., Journal of Controlled Release, 60, 149-160 (1999).
Godbey et al., PNAS USA, 96, 5177-5181 (1999).
Ignatov et al., J. Neurosci. 23:907-914 (2003).
Karle et al., Eur. J. Pharmacol., 340(213), 153 (1997).
Karni et al.., Proc. Natl. Acad. Sci. USA, 88:4966-4970 (1991).
Karni et al., Nature, 365:250-252 (1993).
Kohler et al., Nature, 256:495 (1975).
Kunath et al., Pharmaceutical Research, 19, 810-817 (2002).
Lotery et al., Age Aging, 29:221-222 (2000).
Nagarajan et al., IEEE Trans. Rehabil. Eng., 6:257-268 (1998).
Ogris et al., AAPA PharmSci, 3, 1-11 (2001).
Peterson et al., Bioconjugate Chem., 13, 845-854 (2002).
Rajakumar et al., Synapse, 26(3), 199 (1997).
Reynolds et al., Nat Biotechnol 22, 326-330 (2004).
Scott et al., J Mol Neurosci 19, 171-177 (2002).
Simantov et al., Neuroscience, 74(1), 39 (1996).
Sommer et al., Antisense Nuc. Acid Drug Dev., 8, 75 (1998).
Thomas et al., PNAS USA, 99, 14640-14645 (2002).
Tully et al., Nat Rev Drug Discov 2, 267-77 (2003).
Wu-pong et al., BioPharm, 12(1), 32 (1999).
Bannai et al., Brain Research, 784(1,2), 304 (1998).

* cited by examiner

*Primary Examiner* — Tracy Vivlemore
(74) *Attorney, Agent, or Firm* — Don J. Pelto; Sheppard, Mullin, Richter & Hampton LLP

(57) ABSTRACT

The present invention provides methods for screening a pharmaceutical agent for its ability to modulate long term memory formation, performance of a hippocampal-dependent cognitive task or Gpr12 function. The present invention also provides methods for modulating long term memory formation or performance of a hippocampal-dependent cognitive task by modulating Gpr12-dependent protein expression. The present invention further provides methods for treating a defect in long term memory formation by inhibiting Gpr12 function and methods for treating a defect in performance of a hippocampal-dependent cognitive task by inhibiting Gpr12 function.

24 Claims, 12 Drawing Sheets

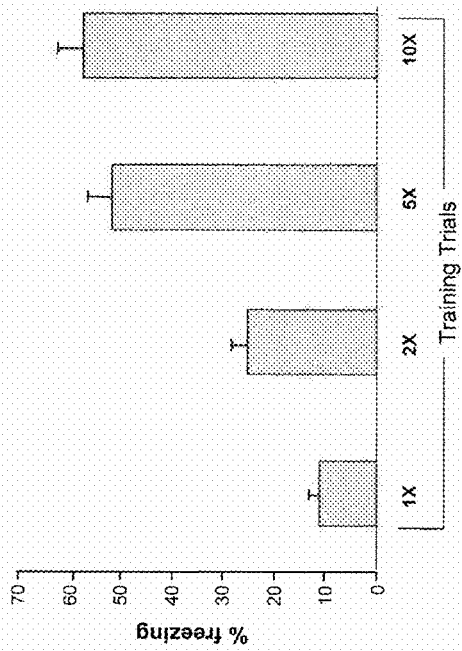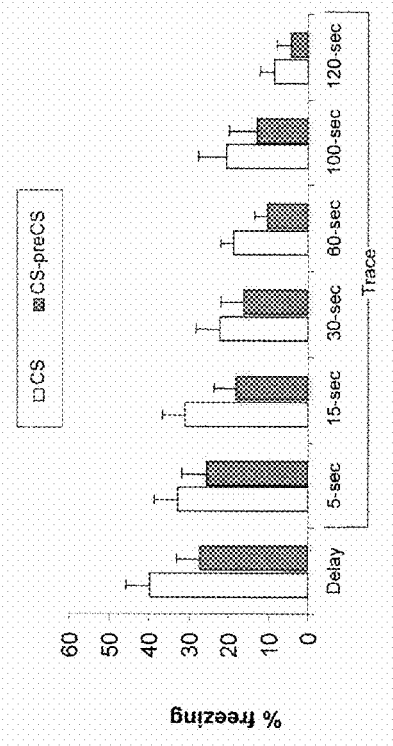
FIG. 1

MOUSE

| Brain | GPR3 | GPR6 | GPR12 |
|---|---|---|---|
| Whole Brain | 222 | 1894 | 173 |
| Hippocampus | 123 | 2075 | 210 |
| Frontal Cortex | 124 | 844 | 245 |
| Cerebral Cortex | 109 | 811 | 172 |
| Thalamus | 75 | 1123 | 827 |
| Cerebellum | 97 | 13 | 414 |
| Hypothalamus | 49 | 544 | 157 |
| Pons | 98 | 38 | 263 |
| Brainstem | 106 | 610 | 725 |
| Medulla | 1 | 1 | 2 |

| Non-Brain | | | |
|---|---|---|---|
| Testis | 38 | 189 | 0 |
| Ovary | 19 | 7 | 1 |
| Uterus | 3 | 1 | 2 |
| Small Intestine | 1 | 8 | 0 |
| Heart | 11 | 23 | 0 |
| Kidney | 6 | 9 | 0 |
| Lung | 3 | 3 | 0 |
| Liver | 1 | 4 | 68 |
| Spleen | 3 | 33 | 1 |
| Thymus | 10 | 2 | 0 |

B

HUMAN

| Brain | GPR3 | GPR6 | GPR12 |
|---|---|---|---|
| Whole Brain | 82 | 51 | 255 |
| Hippocampus | 65 | 34 | 234 |
| Frontal Cortex | 99 | 73 | 203 |
| Cerebral Cortex | 108 | 54 | 182 |
| Cerebellum | 96 | 4 | 201 |
| Pons | 230 | 3 | 48 |
| Medulla | 86 | 2 | 55 |

| Non-Brain | | | |
|---|---|---|---|
| Testis | 7 | 15 | 15 |
| Ovary | 5 | 29 | 0 |
| Uterus | 2 | 2 | 1 |
| Placenta | 4 | 15 | 9 |
| Small Intestine | 6 | 0 | 31 |
| Skeletal Muscles | 1 | 0 | 4 |
| Thymus | 5 | 2 | 1 |
| Blood | 19 | 0 | 1 |
| Pancreas | 1 | 1 | 0 |

Figure 4: Effect of Gpr12 knockdown in hippocampus (A) and amygdala (B) on contextual fear memory.

Figure 6: Nissl stain of non-targeting and Gpr12 siRNA infused hippocampus. Hippocampal slices dorsal and ventral of the cannula insertion site are shown.

FIG. 9
A 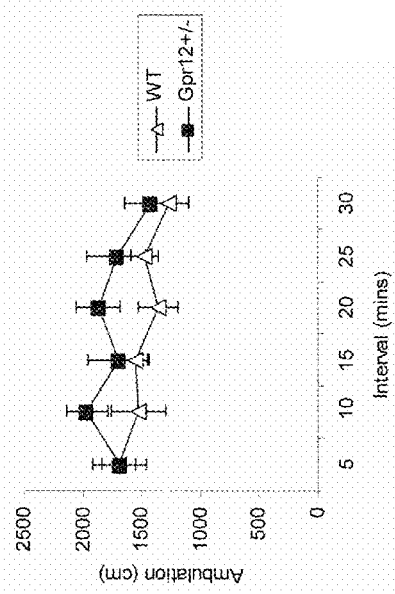
B 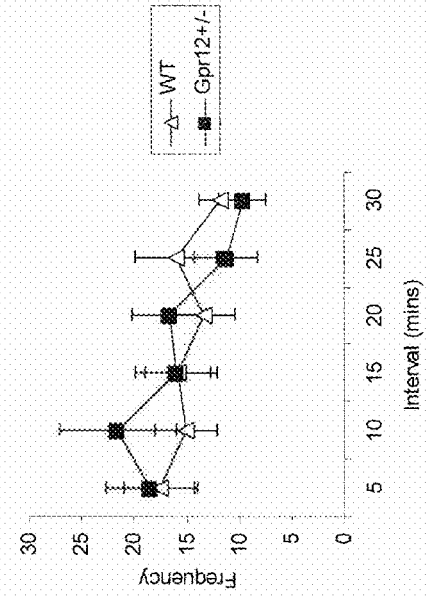

FIG. 11
A 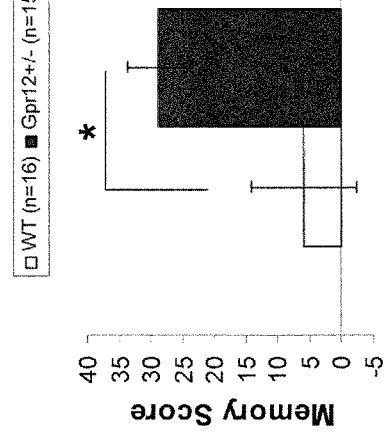
B 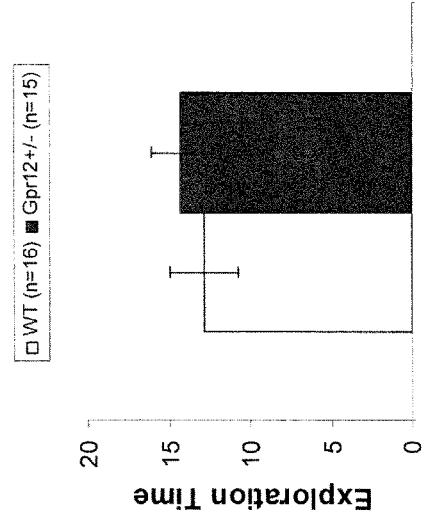

FIG. 12
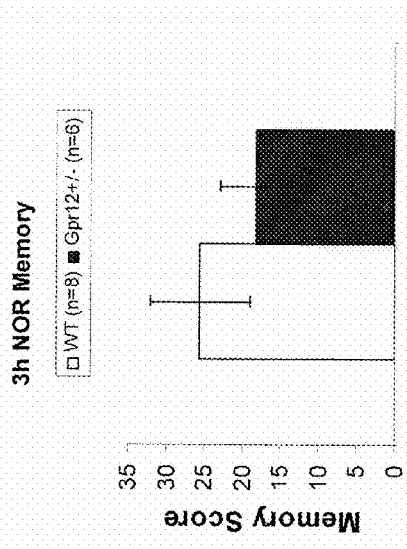
A
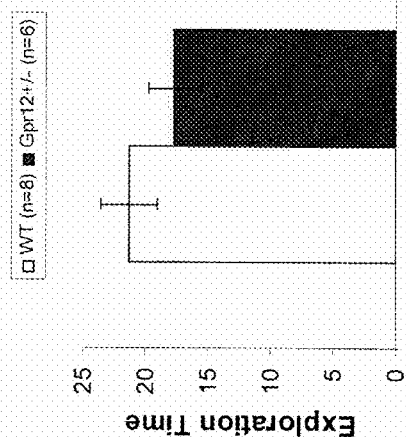
B

METHODS OF ENHANCING LONG TERM MEMORY FORMATION BY INHIBITION OF GPR12

RELATED APPLICATION

This application claims the benefit, under 35 U.S.C. §119, of provisional U.S. Application Ser. No. 60/938,163, filed May 15, 2007, the entire contents and substance of which is hereby incorporated by reference.

FIELD OF THE INVENTION

The present invention relates to methods of treating cognitive disorders by inhibition of the Gpr12 gene or gene products.

BACKGROUND OF THE INVENTION

An attribute that many organisms, including humans, possess is memory of past events. This attribute has been studied for many decades with much information now available that explains many of its ramifications. For example, two basic types of memory have been identified: transcription-independent memory, which includes short term memory, and transcription-dependent memory, which includes long term memory.

Gpr12 is an orphan GPCR. Analysis of Gpr12 expression by in situ hybridization revealed that Gpr12 is widely expressed in the mouse CNS, with highest levels of expression within hippocampus and thalamus. (Ignatov et al., 2003, J. Neurosci. 23:907-914). The endogenous ligand of Gpr12 is unknown. Phylogenetic analysis of Gpr12 revealed the orphan receptors Gpr3 and Gpr6 as closest homologous of Gpr12. The subgroup comprising the three orphan GPCRs is most closely related to the Mcr (melanocortin-like peptide) and Edg (endothelial differentiation) families of GPCRs. This indicates lipids or peptides as possible ligand for Gpr12. Sphingosylphosphorylcholine (SPC) activates Gpr12 in heterologous expression systems. SPC promotes differentiation and maturation of cultured embryonic cortical neurons Id. However the endogenous ligand of Gpr12 and its in vivo function in the adult CNS are unknown.

Previous results showed that Gpr12 signals via a $G\alpha_i$ dependent mechanism. Id. The cAMP/PKA pathway regulates CREB activity and long-term memory in the mammalian brain (Abel et al., 1997, Cell 88:615-626), (Bourtchouladze et al., 1998, Learn Mem. 5:365-374), (Barad et al., 1998, Proc. Natl. Acad. Sci USA 95:15020-15025), (Bourtchouladze et al., 2003, Proc. Natl. Acad. Sci USA 100:10518-10522).

SUMMARY OF THE INVENTION

It has been discovered that the g-coupled protein receptor Gpr12 plays an important role in mediating the cellular events underlying memory formation in mammals. As described herein, Gpr12-mediated mRNA trafficking within the hippocampus has been discovered to be important for contextual long-term memory formation in mammals. It has been discovered that disruption or inhibition of hippocampal Gpr12 function enhances transcription dependent memory formation (such as long term memory formation) in mammals. The present application is directed to, inter alia, methods of treating long term memory defects or cognitive disorders by the inhibition of the Gpr12 gene or gene products.

The invention provides methods for modulating cognitive function in a mammal. In one embodiment the invention is directed to a method comprising administering to a mammal an effective amount of a pharmaceutical agent which modulates Gpr12 activity in the mammal.

In another embodiment the mammal is an adult mammal. In another embodiment the mammal is a human.

In another embodiment the administering results in long term memory formation modulation. In another embodiment long term memory formation is enhanced.

In another embodiment the methods further comprises detecting the modulation in the long term memory formation. In another embodiment the detecting of the modulation is the detection of modulation of a hippocampal-dependent cognitive task. In another embodiment the detecting of the modulation is the detection of modulation of an amygdala-dependent cognitive task. In another embodiment the detecting of the modulation is the detection of modulation of a hippocampal-dependent cognitive task and an amygdala-dependent cognitive task.

In particular embodiments, the modulation of Gpr12 activity comprises modulation of Gpr12 protein expression in the mammal. In additional embodiments, the administering results in enhancement of cognitive function.

In another embodiment the methods further comprise training the mammal under conditions sufficient to produce an improvement in performance of a particular cognitive task.

In another embodiment a performance gain is achieved relative to the performance of the cognitive task achieved by training alone in the absence of the administering.

In another embodiment the training comprises multiple training sessions. In another embodiment the training comprises spaced training sessions.

In another embodiment the pharmaceutical agent is administered before an or during each training session.

In another embodiment the pharmaceutical agent comprises one or more of an effective amount of a Gpr12 siRNA molecule, an effective amount of a biologically active Gpr12 antisense fragment and/or an effective amount of an antibody specific for the Gpr12 protein.

Another method according to the present invention comprises the steps of: (a) introducing a pharmaceutical agent of interest into host cells expressing a Gpr12 protein; and (b) determining Gpr12 function, wherein a difference in the Gpr12 function determined in (b) compared to the Gpr12 function of host cells of (a) to which the pharmaceutical agent has not been administered identifies the pharmaceutical agent as one capable of modulating Gpr12 function.

Another method according to the present invention comprises the steps of: (a) administering to a mammal a pharmaceutical agent which modulates Gpr12 function; (b) training the mammal of step (a) and a control mammal of the same species to which the pharmaceutical agent has not been administered under conditions sufficient to produce long term memory formation in the mammal; (c) assessing long term memory formation in the mammals trained in step (b); and (d) comparing long term memory formation in the mammals assessed in step (c), wherein a difference in long term memory formation assessed in the mammal administered the pharmaceutical agent relative to long term memory formation assessed in the control mammal identifies the pharmaceutical agent as one which is capable of modulating long term memory formation.

In a particular embodiment the mammals are adult mammals. In another particular embodiment the mammals are humans.

In another embodiment the long term memory formation is hippocampus-dependent long term memory formation. In another embodiment the long term memory formation is amygdala-dependent long term memory formation. In another embodiment the long term memory formation is hippocampus-dependent and amygdala-dependent long term memory formation.

In another embodiment the modulation of Gpr12 activity comprises modulation of Gpr12 protein expression in the mammal.

In another embodiment the training comprises multiple training sessions. In another embodiment the training comprises spaced training sessions.

In yet another embodiment the pharmaceutical agent is administered before and, or during each training session.

In another embodiment the pharmaceutical agent comprises one or more of an effective amount of a Gpr12 siRNA molecule, an effective amount of a biologically active Gpr12 antisense fragment and/or an effective amount of an antibody specific for the Gpr12 protein.

These and other aspects of the invention will become evident upon reference to the following detailed description and attached drawings. It is to be understood however that various changes, alterations and substitutions may be made to the specific embodiments disclosed herein without departing from their essential spirit and scope. In addition, it is further understood that the drawings are intended to be illustrative and symbolic representations of an exemplary embodiment of the present invention and that other non-illustrated embodiments are within the scope of the invention.

BRIEF DESCRIPTION OF THE FIGURES

FIG. 1a is a bar graph showing the effect of number of trials on contextual memory formation. Mice were trained with increasing numbers of CS-US pairings ad contextual memory assessed 4 days later.

FIG. 1b is a bar graph showing the effect of the trace interval on temporal memory formation. Mice were trained in trace fear conditioning using increasingly long trace intervals and tone memory compared to delay conditioning.

FIG. 2a is a table of the level of Gpr12 mRNA expression within mouse CNS as measured by real-time PCR.

FIG. 2b is a table of the level of Gpr12 mRNA expression within mouse CNS as measured by real-time PCR.

FIG. 9a shows general motor and exploratory activity in the open field and particularly horizontal activity (ambulation) in Gpr12+/- mice (n=9) and WT controls (n=8).

FIG. 9b shows general motor and exploratory activity in the open field and particularly vertical activity (rearing) in Gpr12+/- mice (n=9) and WT controls (n=8).

FIG. 11a shows 24 hour retention of NOR memory in Gpr12+/- mice (n=15) and WT controls (n=16).

FIG. 11b shows exploration time during testing in Gpr12+/- mice and WT controls.

FIG. 12a shows 3 hour retention of NOR memory in Gpr12+/- mice (n=6) and WT controls (n=8).

FIG. 12b shows exploration time during testing.

DETAILED DESCRIPTION OF THE INVENTION

Figure 3:
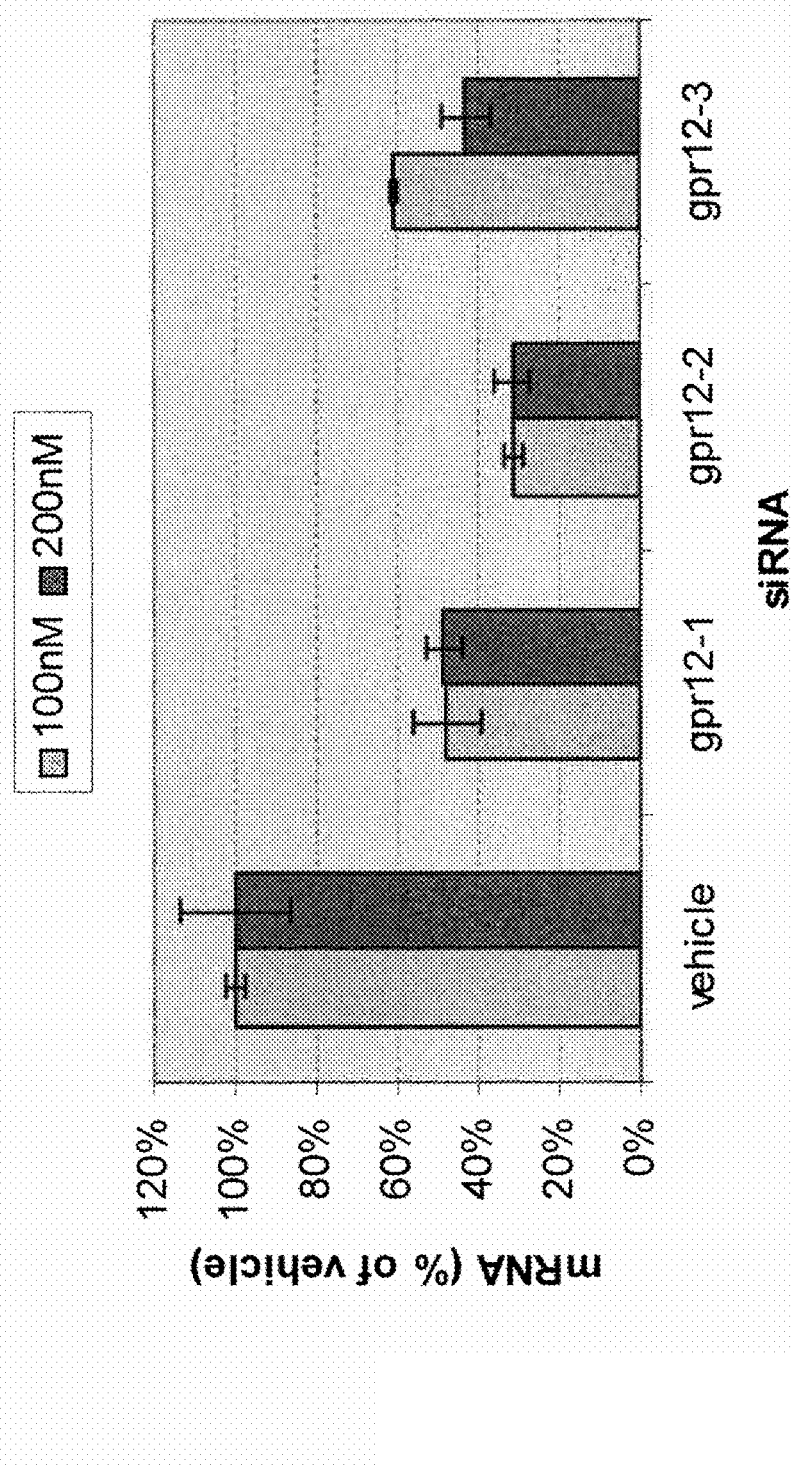
FIG. 3 is a bar graph of the mRNA levels of Gpr12 24 hours after siRNA treatment in Neuro2A cells.

The present invention is related to the discovery that inhibition of Gpr12 can promote long term memory formation.

Transcription-independent memory includes various "memory phases", such as short-term memory, intermediate- (or middle-) term memory and (in flies) anesthesia-resistant memory. In common to these forms is that pharmacological inhibitors of RNA transcription do not disrupt these memories. Transcription-dependent memory usually is referred to as long-term memory and inhibitors of RNA synthesis block its appearance.

Memory formation of this specific, experimental experience can exist in two general forms: a transcription-independent form and a transcription-dependent form. The former includes various "memory phases," such as short-term memory, and intermediate- (or middle-) term memory. In common to these forms is that pharmacological inhibitors of RNA transcription do not disrupt these memories. The latter form usually is referred to as long-term memory and inhibitors of RNA synthesis block its appearance.

It has been discovered that the g-coupled protein receptor Gpr12 plays an important role in mediating the cellular events underlying memory formation in mammals. As described herein, Gpr12-mediated mRNA trafficking within the hippocampus has been discovered to be important for contextual long-term memory formation in mammals. It has been discovered that disruption or inhibition of hippocampal Gpr12 function enhances transcription dependent memory formation (such as long term memory formation) in mammals. The present direction is directed to methods of treating long term memory defects or cognitive disorders by the inhibition of the Gpr12 gene or gene products.

Unless defined otherwise, technical and scientific terms used herein have the same meaning as commonly understood by one of skill in the art to which this invention belongs.

One skilled in the art will recognize many methods and materials similar to equivalent to those described here, which could be used in the practice of this invention. Indeed the present invention is no way limited to the methods and materials described herein. For the purposes of the present invention, the following terms are defined.

DEFINITIONS

The term "animal", as used herein, includes mammals, as well as other animals, vertebrate and invertebrate (e.g., birds, fish, reptiles, insects (e.g., *Drosophila* species), Aplysia). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses). Preferably the mammal is a human.

As used herein, a control animal" or a "normal animal" is an animal that is of the same species as, and otherwise comparable to (e.g., similar age, sex), the animal that is trained under conditions sufficient to induce transcription-dependent memory formation in that animal.

By "Gpr12 function" is meant the biological activity of Gpr12. Biological activity is understood to mean biological function or action.

The term "Gpr12" inhibitor" or GPR12 inhibitor compound or agent" means a compound capable of acting as an antagonist of the Gpr12 polypeptide and capable of either directly or indirectly inhibiting the function of the Gpr12 polypeptide. Such compounds include interfering RNA (siRNA) specific for the Gpr12 gene, antisense nucleotides specific for the Gpr12 gene, antibodies specific for the Gpr12 protein and small molecules, including peptides.

The Gpr12 gene and protein sequences of mouse and humans are presented in Table 1.

TABLE 1

GRP12 genes and proteins

| Name | Accession | SEQ ID NO: | Sequence |
|---|---|---|---|
| Mouse Gpr12 protein | NP_001010941 | 1 | mnedpkvnls glprdcidag apenisaavp sqgsvaesep elvvnpwdiv lcssgtlicc enavvvliif hspslrapmf lligslalad llaglgliin fvfayllqse atklvtigli vasfsasvcs llaitvdryl slyyaltyhs ertvtftyvm lvmlwgtsic lgllpvmgwn clrdestcsv vrpltknnaa ilsisflfmf almlqlyiqi ckivmrhahq ialqhhflat shyvttrkgv stlalilgtf aacwmpftly sliadytyps iytyatllpa tynsiinpvi yafrnqeiqk alcliccgci psslsqrars psdv |
| Mouse Variant 1 mRNA | NM_001010941 | 2 | aagggaacaa taatccgcag accggccaac tgcaatctaa gagagggagt cgcttgctgt tgtaagtctc ctccgccagc cctaacctgc ttacccgca ttcctcctgt tcatcccgaa aacccggccg tttacaattc tttagggaa agcataagaa gccgagcccc agggtcaagg gcgcctcggg gaagccacag gatcaaagta ggtcgccaga ctctccggcc gttcgagtgg gtcttcgcat gactgttgca ggcgggcgtc cacggtggcg ggctcccgcc cctcacgcag ctgcgacctg cggggcgcg cgcagcctcg tggggtccc gcggatgcgc gccggcggg gagcgcggag ggcggagagc cgggcgcgag caccgcagct cacctgccgc gggcgccacc acggacgtgc cacgcgggtg gcccgagcta ttcggcagca ctgaaggagc caccctcgg ccagggcgtg ccaaggacag gggttaaaat gaacgacgac ccgaaggtca atttaagcgg gctgcctcgg gactgtatag atgccggtgc tccagagaac atctcagccg ctgtccctc ccagggctct gttgcggagt cagaacccga gctcgttgtc aacccctggg acattgtctt gtgcagctca ggaaccctca tctgctgtga aaatgccgtt gtggtcctta tcatcttcca cagcccagc ctgcgagccc ccatgttcct actgataggc agcctggctc ttgcagacct gctggctggc ctgggactca tcatcaattt tgttttgcg tacctgcttc agtcagaagc caccaagctg gtcaccatcg gactcattgt cgcctctttc tctgcctctg tctgcagttt gctggctatt actgtggacc gctacctctc gctatattac gccctgacgt accactccga gaggaccgtc acctttacct atgtcatgct agtgatgctc tggggaacct ccatctgcct ggggccgctg cccgtcatgg gctggaactg cttgagggac gagtccacct gcagcgtggt cagacctctc actaagaaca acgctgccat cctctccata tccttcctct tcatgtttgc tctgatgctt cagctctaca tccagatttg taagattgtg atgaggcacg cccatcagat agccctgcag caccacttcc tggctacatc gcactatgtg actacccgga aaggggtctc gaccctggct ctcatcctag ggaccttttgc tgcctgctgg atgcctttca ccctctattc cttgatcgcc gattacacct acccttcgat ctataccat gccaccctcc tgcccgccac ctacaattcc atcatcaacc ctgtcattta cgctttcaga aaccaagaga tccagaaagc cctctgcctc atttgctgtg ggtgcatccc ttcctcgctg tctcagagag ctcggtctcc cagcgatgtg tagcagcctt ctcctcatag gacgctgcct ctaccaagcg ctcccacctc ccagggcggc cagtgatttc cttccttaaa ttcttttgcac tggatctcac aagcagaagc aatgacatct tttagacacg tattgacagt ggaaatcatc ttaccagtgt tttttaaaa aaaaacaaaa caaaactcga cttctcggct cagcattctg ttgtttggtt tgggagttag gatttgtttg tttgtttgct tgtttgtttg tttggagggt gtaatgggac ctcatgtggc catgaaatta tacaaaagtc tcgggatttt ttaacctagg cttgaaaata aatcaaagtt ttaaaggaaa ctggagaagg aaatactttt tctgaaggaa atactttttt tttttaatc aaggtagatc ttccactctg tatgtatcta acaggatagg agcttgtcca tataaccaaa atagtttata taattacatt tggaagggct tgtgtttatt tctaggaatt cagtaataag tgaccagtaa cagaggcgcg aactccttc tttcctttca gcagtagtga ctgctcttaa gaatcacttt gcagttctc tgtgttacag tttggtatgc atggttacct gtggtagtca gatcactaat tgcaatattg ccatgttaaa cccagaatta aaagagtcat ttttcttca atacagtttt tgaaatacc ttcaaagt gagtcatgaa aaaaatgttt ccaattacat atgagatagc actggttaga tttgtcattg tgattttaa aactctagac tggtggtttt cagaaaacaa aagagaaaat attaacagca tctattgaaa gaagatttta tttattttta atatattctg agagaataaa tggtgtgata ctattaagaa atatacaaac atgactttc aaatctctaa aaaaaaaaaa aaaaa |
| Mouse variant 2 mRNA | NM_008151 | 3 | cggcatggga gatgcaatta gccaatgtcg gttttcagcg ttttggcaag tgtgcgagtg tgcatgtgcc gcctcggag tcctgatccg tgtttccctc agagacaaac agcatttcgg ttcagactt tagcttttgt ttttaattcc tgaagtcgt ggcatttga cactgatagc tgagcccagg gttgtctgtc cttctctgtg tgttttgcat gatcttggat tggcaccta ctgtacccaa acattaaaaa gcctgtcttt ccgttgaaga ggacagggt taaaatgaac gaagacccga aggtcaactt aagcgggctg cctcgggact gtatagatgc cggtgctcca gagaacatct cagccgctgt ccccccccag ggctctgttg cggagtcaga acccgagctc |

TABLE 1-continued

GRP12 genes and proteins

| Name | Accession | SEQ ID NO: | Sequence |
|---|---|---|---|
| | | | gttgtcaacc cctgggacat tgtcttgtgc agctcaggaa ccctcatctg ctgtgaaaat |
| | | | gccgttgtgg tccttatcat cttccacagc cccagcctgc gagccccat gctcctactg |
| | | | ataggcagcc tggctctcgc agacctgctg gctggcctgg gactcatcat caattttgtt |
| | | | tttgcgtacc tgcttcagtc agaagccacc aagctggtca ccatcggact cattgtcgcc |
| | | | tctttctctg cctctgtctg cagtttgctg gctattactg tggaccgcta cctctcgcta |
| | | | tattacgccc tgacgtacca ctccgagagg accgtcacct ttacctatgt catgctagtg |
| | | | atgctctggg gaacctccat ctgcctgggg ctgctgcccg tcatgggctg gaactgcttg |
| | | | agggacgagt ccacctgcag cgtggtcaga cctctcacta agaacaacgc tgccatcctc |
| | | | tccatctcct tcctcttcat gtttgctctg atgcttcagc tctacatcca gatttgtaag |
| | | | attgtgatga ggcacgccca tcagatagcc ctgcagcacc acttcctggc tacatcgcac |
| | | | tatgtgacta cccggaaagg ggtcccgacc ctggctctca tcccagggac ctttgctgcc |
| | | | tgctggatgc cttttcaccct ctatcccttg atcgccgatt acacctaccc ttcgacctat |
| | | | acctatgcca ccctcctgcc cgccacctac aattccatca tcaaccctgt catttacgct |
| | | | ttcagaaacc aagagatcca gaaagccctc tgcctcattt gctgtgggtg catcccttcc |
| | | | tcgctgtctc agagagctcg gtctcccagc gatgtgcagc agccttctcc tcataggacg |
| | | | ctgcctctac caagcgctcc cacctcccag ggcggccagt gatttccttc cttaaattct |
| | | | ttgcactgga tctcacaagc agaagcaatg acatctttta gacacgtatt gacagtggaa |
| | | | atcatcttac cagtgttttt taaaaaaaaa acaaaacaaa actcgacttc tcggctcagc |
| | | | attctgttgt ttggtttggg agttaggatt tgtttgtttg tttgcttgtt tgtttgtttg |
| | | | gagggtgtaa tgggacctca tgtggccatg aaattataca aagtctcgg gattttttaa |
| | | | cctaggcttg aaaataaatc aaagttttaa aggaaactgg agaaggaaat actttttctg |
| | | | aaggaaatac tttttttttt ttaatcaagg tagatcttcc attctgtatg tatctaacag |
| | | | gataggagct ttgccatata accaaaatag tttacataat tacatttgga agggcttgtg |
| | | | tttatttcta ggaattcagt aataagtgac cagtaacaga ggcgcgaact cctttatttc |
| | | | ctttcagcag tagtgactgc tcttaagaat cactttgcag tttctctgtg ttacagtttg |
| | | | gtatgcatgg ttacctgtgg tagtcagatc actaattgca atattgccat gttaaaccca |
| | | | gaattaaaag agtcattttt tcttcaatac agttttgaa atatcctttc caaagtgagt |
| | | | catgaaaaaa atgttccaa ttacatatga gatgcactg gttagatttg tcattgtgat |
| | | | ttttaaaact ctagactggt ggttttcaga aaacaaaaga gaaatatta acagcatcta |
| | | | ttgaaagaag attttattta tttttaatat attctgagag aataaatggt gtgatactat |
| | | | taagaaatat acaaacatga cttttcaaat ctctaaaaaa aaaaaaaaaa a |
| Mouse Gpr12 protein | NP_032177 | 4 | mnedpkvnls glprdcidag apenisaavp sqgsvaesep elvvnpwdiv lcssgtlicc enavvvliif hspslrapmf lligslalad llaglgliin fvfayllqse atklvtigli vasfsasvcs llaitvdryl slyyaltyhs ertvtftyvm lvmlwgtsic lgllpvmgwn clrdestcsv vrpltknnaa ilsisflfmf almlqlyiqi ckivmrhahq ialqhhflat shyvttrkgv stlalilgtf aacwmpftly sliadytyps iytyatllpa tynsiinpvi yafrnqeiqk alcliccgci psslsqrars psdv |
| Human Gpr12 mRNA | NM_005288 | 5 | atgaatgaag acctgaaggt caatttaagc gggctgcctc gggattattt agatgccgct gctgcggaga acatctcggc tgctgtctcc tcccgggttc ctgccgtaga gccagagcct gagctcgtag tcaaccccctg ggacattgtc ttgtgtacct cgggaaccct catctcctgt gaaaatgcca ttgtggtcct tatcatcttc cacaaccccca gcctgcgagc acccatgttc ctgctaatag gcagcctggc tcttgcagac ctgctggccg gcattggact catcaccaat tttgtttttg cctacctgct tcagtcagaa gccaccaagc tggtcacgat cggcctcatt gtcgcctctt tctctgcctc tgtctcagc ttgctggcta tcactgttga ccgctacctc tcactgtact acgctctgac gtaccattcg gagaggacgg tcacgttttac ctatgtcatg ctcgtcatgc tctggggac ctccatctgc ctggggctgc tgcccgtcat gggctggaac tgcctccgag acgagtccac ctgcagcgtg tcagaccgc tcaccaagaa caacgcggcc atcctctcgg tgtccttcct cttcatgttt gcgctcatgc ttcagctcta catccagatc tgtaagattg tgatgaggca cgcccatcag atagccctgc agcaccactt cctggccacg tcgcactatg tgaccacccg gaaaggggtc tccacctgg ctatcatcct ggggacgttt gctgcttgct ggatgccttt caccctctat tccttgatag cggattacac ctaccccctcc atctatacct acgccaccct cctgcccgcc acctacaatt ccatcatcaa ccctgtcata tatgctttca gaaaccaaga gatccagaaa gcgctctgtc tcatttgctg cggctgcatc ccgtccagtc tcgcccagag agcgcgctcg cccagtgatg tgtag |
| Human Gpr12 protein | NP_005279 | 6 | mnedlkvnls glprdyldaa aaenisaavs srvpavepep elvvnpwdiv lctsgtlisc enaivvliif hnpslrapmf lligslalad llagigliin fvfayllqse atklvtigli vasfsasvcs llaitvdryl slyyaltyhs ertvtftyvm lvmlwqtsic lgllpvmgwn clrdestcsv vrpltknnaa ilsvsflfmf almlqlyiqi ckivmrhahq ialqhhflat shyvttrkgv stlaiilgtf aacwmpftly sliadytyps iytyatllpa tynsiinpvi yafrnqeiqk alcliccgci psslaqrars psdv |

In various species, long-term memory (LTM) is defined by two main biological properties. First, formation of long-term memory requires synthesis of new proteins. Second, it involves cAMP-responsive transcription and is mediated through the cAMP-response element binding protein (CREB) family transcription factors.

"Cognitive disorders, defects or conditions" include age-associated memory impairment, neurodegenerative diseases (e.g., Alzheimer's disease, Parkinson's disease, Huntington's disease (chorea), other senile dementia), psychiatric diseases (e.g., depression, schizophrenia, autism, attention deficit disorder), trauma dependent loss of function (e.g., cerebrovascular diseases (e.g., stroke, ischemia), brain tumor, head or brain injury), genetic defects (e.g., Rubinstein-Taybi syndrome, down syndrome, Angelman syndrome, neurofibromatosis, Coffin-Lowry syndrome, Rett syndrome, myotonic dystrophy, fragile X syndrome (e.g., fragile X-1, fragile X-2), William's syndrome) and learning disabilities.

Formal cognitive training protocols are known and readily available in the art. See for example, Karni, A. and Sagi, D., "Where practice makes perfect in text discrimination: evidence for primary visual cortex plasticity", Proc. Natl. Acad. Sci. USA, 88:4966-4970 (1991); Karni, A. and Sagi, D., "The time course of learning a visual skill", Nature, 365:250-252 (1993); Kramer, A. F. et al., "Task coordination and aging: explorations of executive control processes in the task switching paradigm", Acta Psychol. (Amst), 101:339-378 (1999); Kramer, A. F. et al., "Training for executive control: Task coordination strategies and aging", In Aging and Skilled Performance: Advances In Theory and Applications, W. Rogers et al., eds. (Hillsdale, N.J.: Erlbaum) (1999); Rider, R. A. and Abdulahad, D. T., "Effects of massed versus distributed practice on gross and fine motor proficiency of educable mentally handicapped adolescents", Percept. Mot. Skills, 73:219-224 (1991); Willis, S. L. and Schaie, K. W., "Training the elderly on the ability factors of spatial orientation and inductive reasoning", Psychol. Aging, 1:239-247 (1986); Willis, S. L. and Nesselroade, C. S., "Long-term effects of fluid ability training in old-age", Develop. Psychol., 26:905-910 (1990); Wek, S. R. and Husak, W. S. "Distributed and massed practice effects on motor performance and learning of autistic children", Percept. Mot, Skills, 68:107-113 (1989); Verhaehen, P. et al., "Improving memory performance in the aged through mnemonic training: a meta-analytic study", Psychol. Aging, 7:242-511 (1992); Verhaeghen, P. and Salthouse, T. A., "Meta-analyses of age-cognition relations in adulthood: estimates of linear and nonlinear age effects and structural models", Psychol. Bull., 122:231-249 (1997); Dean, C. M. et al., "Task-related circuit training improves performance of locomotor tasks in chronic stroke: a randomized, controlled pilot trial", Arch. Phys. Med. Rehabil., 81:409-417 (2000); Greener, J. et al., "Speech and language therapy for aphasia following stroke", Cochrane Database Syst. Rev., CD000425 (2000); Hummelsheim, H. and Eickhof, C., "Repetitive sensorimotor training for arm and hand in a patient with locked-in syndrome", Scand. J. Rehabil. Med., 31:250-256 (1999); Johansson, B. B., "Brain plasticity and stroke rehabilitation. The Willis lecture", Stroke, 31:223-230 (2000); Ko Ko. C., "Effectiveness of rehabilitation for multiple sclerosis", Clin. Rehabil., 13 (Suppl. 1):33-41 (1999); Lange, G. et al., "Organizational strategy influence on visual memory performance after stroke: cortical/subcortical and left/right hemisphere contrasts", Arch. Phys. Med. Rehabil., 81:89-94 (2000); Liepert, J. et al., "Treatment-induced cortical reorganization after stroke in humans", Stroke, 31:1210-1216 (2000); Lotery, A. J. et al., "Correctable visual impairment in stroke rehabilitation patients", Age Ageing, 29:221-222 (2000); Majid, M. J. et al., "Cognitive rehabilitation for memory deficits following stroke" (Cochrane review), Cochrane Database Syst. Rev., CD02293 (2000); Merzenich, M. et al., "Cortical plasticity underlying perceptual, motor, and cognitive skill development: implications for neurorehabilitation", Cold Spring Harb. Symp. Quant. Biol., 61:1-8 (1996); Merzenich, M. M. et al., "Temporal processing deficits of language-learning impaired children ameliorated by training", Science, 271:77-81 (1996); Murphy, E., "Stroke rehabilitation", J. R. Coll. Physicians Lond., 33:466-468 (1999); Nagarajan, S. et al. "Speech modifications algorithms used for training language learning-impaired children", IEEE Trans. Rehabil. Eng., 6:257-268. (1998); Oddone, E. et al., "Quality Enhancement Research Initiative in stroke: prevention, treatment, and rehabilitation", Med. Care 38:192-1104 (2000); Rice-Oxley, M. and Turner-Stokes, L., "Effectiveness of brain injury rehabilitation", Clin. Rehabil., 13(Suppl 1):7-24 (1999); Tallal, P. et al., "Language learning impairments: integrating basic science, technology, and remediation", Exp. Brain Res., 123:210-219 (1998); Tallal, P. et al., "Language comprehension in language-learning impaired children improved with acoustically modified speech", Science, 271: 81-84 (1996); Wingfield, A. et al., "Regaining lost time: adult aging and the effect of time restoration on recall of time-compressed speech", Psychol. Aging, 14:380-389 (1999), which references are incorporated herein in their entirety by reference.

Training can comprise one or multiple training sessions and is training appropriate to produce an improvement in performance of the cognitive task of interest. For example, if an improvement in language acquisition is desired, training would focus on language acquisition. If an improvement in ability to learn to play a musical instrument is desired, training would focus on learning to play the musical instrument. If an improvement in a particular motor skill is desired, training would focus on acquisition of the particular motor skill. The specific cognitive task of interest is matched with appropriate training.

By "multiple training sessions" is meant two or more training sessions. The Gpr12 inhibitor can be administered before, during or after one or more of the training sessions. In a particular embodiment, the Gpr12 inhibitor is administered before and during each training session. By "training" is meant cognitive training.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated siRNA molecule. In another embodiment, inhibition, down-regulation, or reduction with siNA molecules is below that level observed in the presence of for example, an siNA molecule with scrambled sequence or with mismatches. In another embodiment, inhibition, down-regulation or reduction with an siRNA molecule is meant that the expression level of the target RNA molecules or equivalent RNA molecules is reduced by at least 20%, 30%, 40%, 50%, 60% or 70% compared to the level in the absence of the siRNA molecules.

By "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal. As a result, long term memory acquisition is faster or better retained. Enhancing performance of a cognitive task refers to the ability to potentiate or improve performance of a specified cognitive task by an animal relative to the normal performance of the cognitive task by the animal.

The term "hippocampal-dependent cognitive task" refers to a cognitive task associated with the hippocampal region of the brain.

The term "amygdala-dependent cognitive task" refers to a cognitive task associated with the amygdala region of the brain.

The term 'target gene" or gene" means, a nucleic acid that encodes an RNA, for example, nucleic acid sequences including, but not limited to, structural genes encoding a polypeptide. The target gene can be a gene derived from a cell or an endogenous gene. By "target nucleic acid" is meant any nucleic acid sequence whose expression or activity is to be modulated. The target nucleic acid can be DNA or RNA.

By "homologous sequence" is meant, a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g. 99%, 98%, 97%, 96%, 95%, 94%, 93%, 92%, 91%, 90%, 89%, 88%, 87%, 86%, 85%, 84%, 83%, 82%, 81%, 80% etc.).

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The term "phosphorothioate" as used herein refers to an internucleotide linkage in an RNA molecule wherein at least one linkage between two nucleotides comprises a sulfur atom. Hence, the term phosphorothioate refers to both phosphorothioate and phosphorodithioate internucleotide linkages.

The term "phosphonoacetate linkage" as used herein refers to an internucleotide linkage in an RNA molecule wherein at least one linkage between two nucleotides comprises an acetyl or protected acetyl group. See for example Sheehan et al., 2003 Nucleic Acids Research 31, 4109-4118 or U.S. Patent Publication No. 2006/0247194

The term "thiophosphonoacetate linkage" as used herein refers to an RNA molecule comprising at least one internucleotide linkage comprising an acetyl or protected acetyl group and a sulfur atom. See for example Sheehan et al., 2003 Nucleic Acids Research 31, 4109-4118 or U.S. Patent Publication No. 2006/0247194

As used herein the term "treating" is intended to mean an amelioration of a clinical symptom indicative of poor long term memory formation. Amelioration of the clinical symptom includes, for example, an increase or improvement in long term memory, an increased ability to perform a cognitive task as compared to pretreatment levels or to an individual without defects in long term memory formation.

As used herein, the term "preventing" is intended to mean a forestalling of a clinical symptom indicative of poor long ter memory formation.

The term "therapeutic efficacy" when used herein, refers to a therapeutic effect of a drag or candidate drug in treating defects in long term memory formation, in improving long term memory formation, in improving the ability to perform cognitive tasks. The therapeutic efficacy can be measured by monitoring the patients ability to perform cognitive tasks.

RNA Molecules

The appropriate siRNA can be produced, for example, either synthetically or by expression in cells. In a one embodiment, the DNA sequences encoding the antisense strand of the siRNA molecule can be generated by PCR. In another embodiment, the siRNA encoding DNA is cloned into a vector, such as a plasmid or viral vector, to facilitate transfer into mammals. In another embodiment, siRNA molecules may be synthesized using chemical or enzymatic means.

In one embodiment of the present invention, each sequence of a siNA molecule of the invention is independently about 18 to about 30 nucleotides in length, in specific embodiments about 18, 19, 20, 21, 22, 23, 24, 25, 26, 27, 28, 29 or 30 nucleotides in length. In one embodiment, the siRNA molecules contain about 19-23 base pairs, and preferably about 21 base pairs. In another embodiment, the siRNA molecules contain about 24-28 base pairs, and preferably about 26 base pairs. Individual siRNA molecules may be in the form of single strands, as well as paired double strands ("sense" and "antisense") and may include secondary structure such as a hairpin loop. Individual siRNA molecules could also be delivered as precursor molecules, which are subsequently altered to give rise to active molecules. Examples of siRNA molecules in the form of single strands include a single stranded anti-sense siRNA against a non-transcribed region of a DNA sequence (e.g. a promoter region). In yet another embodiment, siNA molecules of the invention comprising hairpin or circular structures are about 35 to about 55 (e.g., about 35, 40, 45, 50 or 55) nucleotides in length, or about 38 to about 44 (e.g., about 38, 39, 40, 41, 42, 43, or 44) nucleotides in length and comprising about 16 to about 22 (e.g., about 16, 17, 18, 19, 20, 21 or 22) base pairs.

The siRNA molecules may comprise a nucleotide fragment which is the sense strand or the antisense strand of DNA sequence encoding for the native mouse or human Gpr12 protein sequences. Preferably the mouse or human Gpr12 protein sequence comprise those of Table 1, selected from the group consisting of SEQ ID NO: 1, SEQ ID NO, 4 or SEQ ID NO:6. The siRNA molecules of the invention may be a nucleotide fragment of the sense strand of the mRNA sequences of the native mouse or human Gpr12 mRNAs as shown in Table 1, selected from the group consisting of SEQ ID NO:2, SEQ ID NO:3, SEQ ID NO:5. The siRNA molecules of the invention may be a sequence which is antisense to of the mRNA sequences of the native mouse or human Gpr12 mRNAs as shown in Table 1, selected from the group consisting of SEQ ID NO:2, SEQ ID NO:3, SEQ ID NO:5.

The discussion that follows discusses the proposed mechanism of RNA interference mediated by short interfering RNA as is presently known and is not meant to be limiting and is not an admission of prior art. Chemically-modified short interfering nucleic acids possess similar or improved capacity to mediate RNAi as do siRNA molecules and are expected to possess improved stability and activity in vivo. Therefore, this discussion is not meant to be limiting only to siRNA and can be applied to siNA as a whole. By "improved capacity to mediate RNAi" or "improved RNAi activity" is meant to include RNAi activity measured in vitro and/or in vivo where the RNAi activity is a reflection of both the ability of the siNA to mediate RNAi and the stability of the siNAs of the invention.

RNA interference refers to the process of sequence specific post-transcriptional gene silencing in animals mediated by short interfering RNAs (siRNAs) (Fire et al., 1998, Nature, 391, 806). The corresponding process in plants is commonly referred to as post-transcriptional gene silencing or RNA silencing and is also referred to as quelling in fingi. The process of post-transcriptional gene silencing is thought to be an evolutionarily-conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, Nature, 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, Genes Dev., 15, 188). In addition, RNA interference can also involve small RNA (e.g., micro-RNA or mRNA) mediated gene silencing, presumably though cellular mechanisms that regulate chromatin structure and thereby prevent transcription of target gene sequences (see for example Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

RNAi has been studied in a variety of systems. Fire et al., 1998, Nature, 391, 806, were the first to observe RNAi in *C. elegans*. Wianny and Goetz, 1999, Nature Cell Biol., 2, 70, describe RNAi mediated by dsRNA in mouse embryos. Hammond et al., 2000, Nature, 404, 293, describe RNAi in *Drosophila* cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in *Drosophila* embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309); however, siRNA molecules lacking a 5'-phosphate are active when introduced exogenously, indicating that 5'-phosphorylation of siRNA constructs may occur in vivo.

In one embodiment, the invention features modified siNA molecules. Examples of modifications contemplated for the phosphate backbone include phosphate backbone modifications comprising one or more phosphorothioate, phosphorodithioate, phosphonates, including methylphosphonate, phosphotriester including alkylphosphotriesters, morpholino, amidate carbamate, carboxyethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, Nucleic Acid Analogues: Synthesis and Properties, in Modern Synthetic Methods, VCH, 331-417, and Mesmaeker et al., 1994, Novel Backbone Replacements for Oligonucleotides, in Carbohydrate Modifications in Antisense Research, ACS, 24-39.

Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003, Nucleic Acds Res. 31:589-595. U.S. Patent Publication No. 2007/0104688). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1, each incorporated herein by reference. Other modifications are disclosed in Herdewijn (2000), Antisense Nucleic Acid Drug Dev. 10:297-310, Eckstein (2000) Antisense Nucleic Acid Drug Dev. 10:117-21, Rusckowski et al. (2000) Antisense Nucleic Acid Drug Dev. 10:333-345, Stein et al. (2001) Antisense Nucleic Acid Drug Dev. 11: 317-25 and Vorobjev et al. (2001) Antisense Nucleic Acid Drug Dev. 11:77-85, each incorporated herein by reference RNA may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art.

Antibodies

Exemplary antibodies include polyclonal, monoclonal, humanized, bispecific, and heteroconjugate antibodies.

The term "antibody" is used in the broadest sense and specifically covers, for example single anti-Gpr12 monoclonal antibodies (including antagonist, and neutralizing antibodies), anti-Gpr12 antibody compositions with polyepitopic specificity, single chain anti-Gpr12 antibodies, and fragments of anti-Gpr12 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10). 1057-1062 [1995]); single-chain antibody molecules; and multispecific antibodies formed from antibody fragments.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The anti-Gpr12 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Gpr12 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The anti-Gpr12 antibodies may, alternatively, be monoclonal antibodies. Monoclonal antibodies may be prepared using hybridoma methods, such as those described by Kohler and Milstein, Nature, 256.495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

As will be understood by those of ordinary skill in the art, various other gene disruption techniques can be used with the present invention. As non-limiting examples, homologous recombination, transgenic expression of dominant-negative gene constructs, transgenic expression of normal gene constructs and any other modification of amino acid sequence in the target gene can be used. Viral vectors may also be used as appropriate to deliver various such gene constructs to brain cells, and such constructs include several which act via the RNAi pathway (short hairpin RNA, double stranded RNA, etc).

Formulations

The Gpr12 inhibitor compound sample can be suitably formulated and introduced into the mammal by any means that allows for a sufficient portion of the sample to enter the cell. For example the inhibitor can be formulated in buffer solutions such as phosphate buffered saline solutions, liposomes, micellar structures, and capsids. Formulations of siRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

In one embodiment, the Gpr12 specific siNA molecules of the invention are formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002 Pharmaceutical Research, 19, 810-817 Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-8544; Erbacher et al., 1999, Journal of Gene Medicine Preprint, 1, 1-18; Godbey et al., 1999, PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; and Sagara, U.S. Pat. No. 6,586,524, incorporated by reference herein.

It can be appreciated that the method of introducing Gpr12 inhibitor molecules into the environment of the cell will depend on the type of cell and the make up of its environment. For example, when the cells are found within a liquid, one preferable formulation is with a lipid formulation such as in lipofectamine and the inhibitor can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate the inhibitor in a buffer or saline solution and directly inject the formulated inhibitor into cells. The direct injection of dsRNA duplexes may also be done. For suitable methods of introducing siRNA see U.S. published patent application No. 2004/0203145 A1, incorporated herein by reference.

The Gpr12 inhibitor comprises a pharmacologically effective amount. A pharmacologically or therapeutically effective amount refers to that amount of a inhibitor effective to produce the intended pharmacological, therapeutic or preventive result. The phrases "pharmacologically effective amount" and "therapeutically effective amount" or simply "effective amount" refer to that amount of an inhibitor effective to produce the intended pharmacological, therapeutic or preventive result. For example, if a given clinical treatment is considered effective when there is at least a 20% reduction in a measurable parameter associated with a disease or disorder) a therapeutically effective amount of a drug for the treatment of that disease or disorder is the amount necessary to effect at least a 20% reduction in that parameter.

Suitable amounts of inhibitor must be introduced and these amounts can be empirically determined using standard methods. Typically, effective concentrations of individual siRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

In general a suitable dosage unit of siRNA will be in the range of about 0.001 to about 0.25 milligrams per kilogram body weight of the recipient per day, or in the range of about 0.01 to about 20 micrograms per kilogram body weight per day, or in the range of about 0.01 to about 10 micrograms per kilogram body weight per day, or in the range of about 0.10 to about 5 micrograms per kilogram body weight per day, or in the range of about 0.1 to about 2.5 micrograms per kilogram body weight per day.

The Gpr12 inhibitor can be administered, in one embodiment of the present invention, once daily. However, the formulation may also be dosed in dosage units containing two, three, four, five, six or more sub-doses administered at appropriate intervals throughout the day. In that case, in one embodiment, the inhibitor contained in each sub-dose must be correspondingly smaller in order to achieve the total daily dosage unit. The dosage unit can also be compounded for a single dose over several days, e.g., using a conventional sustained release formulation which provides sustained and consistent release of the siRNA over a several day period. Sustained release formulations are well known in the art. In this embodiment, the dosage unit contains a corresponding multiple of the daily dose. Regardless of the formulation, the pharmaceutical composition must contain inhibitor in a quantity sufficient to inhibit expression of the Gpr12 gene in the animal.

Data can be obtained from cell culture assays to formulate a suitable dosage range. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. Levels of inhibitor in plasma may be measured by standard methods, for example, by high performance liquid chromatography.

The method can be carried out by addition of the siRNA compositions to any extracellular matrix in which cells can live provided that the siRNA composition is formulated so that a sufficient amount of the siRNA can enter the cell to exert its effect. For example, the method is amenable for use with cells present in a liquid such as a liquid culture or cell growth media, in tissue explants, or in whole organisms, including animals, such as mammals and especially humans.

Delivery Methods

DNA sequences encoding an antisense strand or a siRNA specific for a target sequence of a gene are introduced into mammalian cells for expression. To target more than one sequence in the gene (such as different promoter region sequences and/or coding region sequences), separate siRNA-encoding DNA sequences specific to each targeted gene sequence can be introduced simultaneously into the cell. In accordance with another embodiment, mammalian cells may be exposed to multiple siRNAs that target multiple sequences in the gene.

The Gpr12 inhibitors of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In one embodiment, the invention features the use of methods to deliver the nucleic acid molecules of the instant invention to the central nervous system and/or peripheral nervous system. Experiments have demonstrated the efficient in vivo uptake of nucleic acids by neurons. As an example of local administration of nucleic acids to nerve cells, Sommer et al., 1998, Antisense Nuc. Acid Drug Dev., 8, 75, describe a study in which a 15 mer phosphorothioate antisense nucleic acid molecule to c-fos is administered to rats via microinjection into the brain. As an example of systemic administration of nucleic acid to nerve cells, Epa et al., 2000, Antisense Nuc. Acid Drug Dev., 10, 469, describe an in vivo mouse study in which beta-cyclodextrin-adamantane-oligonucleotide conjugates were used to target the p75 neurotrophin receptor in neuronally differentiated PC12 cells. Following a two week course of IP administration, pronounced uptake of p75 neurotrophin receptor antisense was observed in dorsal root ganglion (DRG) cells. In addition, a marked and consistent down-regulation of p75 was observed in DRG neurons. Additional approaches to the targeting of nucleic acid to neurons are described in Broaddus et al., 1998, J. Neurosurg., 88(4), 734; Karle et al., 1997, Eur. J. Pharmocol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; Simantov et al., 1996, Neuroscience, 74(1), 39. Nucleic acid molecules of the invention are therefore amenable to delivery to and uptake by neural cells.

The delivery of nucleic acid molecules of the invention, targeting the candidate gene is provided by a variety of different strategies. Traditional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers. Furthermore, gene therapy approaches, for example as described in Kaplitt et al., U.S. Pat. No. 6,180,613 and Davidson, WO 04/013280, can be used to express nucleic acid molecules in the CNS.

The term "introducing" encompasses a variety of methods of introducing DNA into a cell, either in vitro or in vivo. Such methods include transformation, transduction, transfection, and infection. Vectors are useful and preferred agents for introducing DNA encoding the siRNA molecules into cells. The introducing may be accomplished using at least one vector. Possible vectors include plasmid vectors and viral vectors. Viral vectors include retroviral vectors, lentiviral vectors, or other vectors such as adenoviral vectors or adeno-associated vectors.

Alternate delivery of siRNA molecules or DNA encoding siRNA molecules into cells or tissues may also be used in the present invention, including liposomes, chemical solvents, electroporation, viral vectors, pinocytosis, phagocytosis and other forms of spontaneous or induced cellular uptake of exogenous material, as well as other delivery systems known in the art.

Suitable promoters include those promoters that promote expression of the interfering RNA molecules once operatively associated or linked with sequences encoding the RNA molecules. Such promoters include cellular promoters and viral promoters, as known in the art. In one embodiment, the promoter is an RNA Pol III promoter, which preferably is located immediately upstream of the DNA sequences encoding the interfering RNA molecule. Various viral promoters may be used, including, but not limited to, the viral LTR, as well as adenovirus, SV40, and CMV promoters, as known in the art.

In one embodiment, the invention uses a mammalian U6 RNA Pol III promoter, and more preferably the human U6snRNA Pol III promoter, which has been used previously for expression of short, defined ribozyme transcripts in human cells (Bertrand et al., 1997; Good et al., 1997). The U6 Pol III promoter and its simple termination sequence (four to six uridines) were found to express siRNAs in cells. Appropriately selected interfering RNA or siRNA encoding sequences can be inserted into a transcriptional cassette, providing an optimal system for testing endogenous expression and function of the RNA molecules.

Expression Measurement

Expression of the Gpr12 gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. The measurements can be made on cells, cell extracts, tissues, tissue extracts or any other suitable source material.

The determination of whether the expression of the Gpr12 gene has been reduced can be by any suitable method that can reliably detect changes in gene expression.

EXAMPLES

Example 1

Contextual and Trace Conditioning

Mice were trained with a contextual conditioning paradigm that induces weak memory (FIG. 1, see also Tully, T., et al., Nat Rev Drug Discov 2, 267-77 (2003)). FIG. 1a shows the effect of number of trials on contextual memory formation. Mice were trained with increasing numbers of CS-US pairings and contextual memory assessed 4 days later. Training with 1× or 2×CS-US pairings induced sub-maximal memory.

Trace conditioning becomes increasingly difficult as the time interval between CS and US increases. Mice were trained in trace fear conditioning using increasingly long trace intervals and tone memory compared to delay conditioning. FIG. 1b shows the effect of the trace interval on temporal memory formation. Trace intervals of 30 sec or longer resulted in poor long-term memory for the tone CS (n=29, n=20, n=25, n=18, n=28, n=16 and n=12 for delay conditioning and trace intervals of 5 sec, 15 see, 30 sec, 60 sec. 100 sec, and 120 sec. respectively). In fact, C57BL/6 mice show poor memory if the trace interval between CS and US is 60 seconds or longer (FIG. 1b).

Example 2

Level of Gpr12 RNA in the Hippocampus of Mice After Training

To assess contextual memory, a standardized contextual fear conditioning task originally developed for evaluation of memory in CREB knock-out mice was used. ((Bourtchouladze et al., 1994 Cell 79, 59-68). On the training day, the mouse was placed into the conditioning chamber (Med Associates, Inc. VA) for 2 minutes before the onset of the unconditioned stimulus (US), a 0.5 mA foot shock of 2 seconds duration. For weak training (2 training trials), the US was repeated two times with a 1 min inter-trial interval between shocks. For strong training (5 training trials), 5 foot shocks were given with a 1 min inter-trial interval between shocks (Bourtchouladze et al., 1998 Learn Mem 5, 365-374); (Scott et al., 2002 J Mol Neurosci 19, 171-177); (Tully et al., 2003 Nat Rev Drug Discov 2, 267-277). Training was performed using an automated software package (Med Associates, Inc., VA), After the last training trial, the mice were left in the conditioning chamber for another 30 sec and were then placed back in their home cages. Contextual memory was tested 24 hrs after training. The mouse was placed into the same training chamber and conditioning was assessed by scoring freezing behavior. Freezing was defined as the complete lack of movement in intervals of 5 seconds ((Fanselow and Bolles, 1979 J Comp Physiol Psychol 93, 736-744); (Bourtchouladze et al., 1994 Cell 79, 59-68); (Bourtchouladze et al., 1998 Learn Mem 5, 365-374). Total testing time lasted 3 minutes. After each experimental subject, the experimental apparatus was thoroughly cleaned with 75% ethanol, water, dried, and ventilated. Each experiment was filmed. All experimenters were blind to the drug and training conditions.

All behavioral experiments were designed and performed in a balanced fashion, meaning that (i) for each experimental condition an equal number of experimental and control mice was used; (ii) each experimental condition was replicated several times, and replicate days were added to generate final number of subjects. The proceeding of each session was filmed. In each experiment, the experimenter was unaware (blind) to the treatment of the subjects during training and testing. Data were analyzed by Student's unpaired t test using a software package (StatView 5.0.1; SAS Institute, Inc). Except where stated, all values in the text and figures are expressed as MEAN±SEM.

For trace conditioning training a standardized mouse contextual fear conditioning equipment (Med Associates, Inc., VA; (Bourtchouladze et al., 1994 Cell 79, 59-68); (Bourtchouladze et al., 1998 Learn Mem 5, 365-374) was used. On the training day, the mouse was placed into the conditioning chamber for 2 minutes before the onset of the conditioned stimulus (CS), a 2800 Hz tone, which lasted for 20 seconds at 75 dB. Sixty seconds after the end of the tone a 0.5 mA shock unconditioned stimulus (US) was delivered to the animal for two seconds. Previous experiments have revealed that this training paradigm induces poor trace fear memory in C57BL/6 mice, and that this memory can be facilitated by enhancers of the CREB pathway. After an additional 30 s in the chamber, the mouse was returned to its home cage. After each experimental subject, the experimental apparatus was thoroughly cleaned with 75% ethanol, water, dried, and ventilated for a few minutes.

Testing was done in a novel chamber located in another procedural room to avoid confounding effects of contextual conditioning. The internal conditioning chamber was removed and replaced with a mouse cage. Different colored tape was placed on the backside of each cage to differentiate one from another. Three different cages were used in rotation in order to decrease the possibility of scent contamination from subject to subject. A 30-watt lamp was placed inside the chamber to insure difference in illumination between training and testing. The cages were cleaned using a soapy solution instead of ethanol. Each test began with two minutes of light only (pre-CS), then 20 seconds of tone presentation (CS), followed by an additional 30 seconds of light only (post-CS). In the same manner as during training, the mice were scored one at a time for "freezing" in five-second intervals, as for contextual conditioning described above. The proceeding of each experiment was filmed. The proportion of the freezing response specific to the auditory memory was determined by subtraction of preCS freezing (non-specific) from CS freezing.

After training and testing hippocampal tissue of mice was pooled. Individual RNA preparations were performed using the QIAgen RNeasy kit (Qiagen) according to the manufacturer's specifications. cDNA was generated using TaqMan Reverse transcriptase kit (Applied Biosystems). The cDNA was analyzed using Affymetrix Gene chip analysis and the relative level of expression to naive mice was obtained. Expression changes at 1 h after trace fear conditioning identified by Affymetrix-chip analysis were confirmed by Nimble-chip analysis (NimbleGen Systems, Madison, Wis., USA). Expression changes at 1 h after contextual fear conditioning (5× training trials) identified by Affymetrix-chip analysis were confirmed by a second Affy-chip analysis and by QPCR.

TABLE 2

| Comparison | Time-point | P value (p < 0.05 for significance) | ES value | pPCR Relative quantity (trained vs. naive) |
|---|---|---|---|---|
| Delay conditioned vs. Naive (caged) | 6 h | 0.0008 | −1.81 | 0.75 |
| Trace conditioned vs. Naive (caged) | 6 h | 0.0383 | NS (p value from qPCR confirmation) | 0.70 |

Table 2: Identification of Gpr12 as a memory regulated gene in hippocampus. P value and ES value (Affymetrix gene-chip analysis) and relative expression to naïve (pPCR confirmation) are shown.

Example 3

Screening for siRNAs Targeting Gpr12 Using, Neuro 2A Cell

Expression profiling by real-time PCR revealed Gpr12 mRNA expression within mouse and human CNS with little expression in peripheral tissues (FIG. 2).

Gpr12 is widely present in the mouse CNS (FIG. 2a), with highest expression levels in thalamus, brainstem, and cerebellum, areas of the brain involved in feeding and the integration of sensory information (thalamus), motor control (cerebellum), and autonomous function (brainstem). High levels of Gpr12 were also observed in hippocampus and neocortex, two brain areas critical to memory formation (Fanselow 2005 J Comp Physiol Psychol 93, 736-744). These results are similar to those observed by in situ hybridization in mouse CNS (Ignatov 2003 J Neurosci 23, 907-914). In mouse, Gpr12 expression was below detection levels in most peripheral tissues, with the exception of the liver.

Within the human CNS Gpr12 expression was highest in hippocampus, the neocortex, and the cerebellum (FIG. 2b).

Gpr3 and Gpr6, the closest homologous of Gpr12, were present in the CNS of both mouse and human (FIG. 2a/b). However, Gpr12 mRNA levels appear to be much higher in human CNS than those of Gpr3 and 6. This is in contrast to the situation in mouse, where Gpr6 expression is very prominent in hippocampus, thalamus and neocortex.

In vivo grade siSTABLE siRNA (Dharmacon Inc., Lafayette, USA) was used for evaluation of Gpr12 function in the mouse CNS. siRNA's were chemically modified to enhance stability. A 21 mer siSTABLE non-targeting siRNA was used as control.

For evaluation of siRNA efficacy, Neuro2A cells were transfected using siGENOME siRNA and Dharmafect 3 (Dharmacon, Lafayette, USA). RNA was isolated at 24 h after transfection and cDNA synthesized as described for hippocampal tissue. Per treatment, three individual RNA preparations and cDNA syntheses were performed. Target mRNA levels were determined in duplicate per cDNA replication and ACT values averaged for each experimental replication (n=3 RNA/cDNA preps; Each represented as the mea of two qPCR determinations).

Three siRNAs were identified that efficiently reduced Gpr12 mRNA in vitro (FIG. 3). siRNA2 reduced Qpr12 mRNA levels to 31% of vehicle control at 24 h after treatment and was chosen for in vivo evaluation of Gpr12. In vivo grade siSTABLE siRNA for Gpr12-2 siRNA was obtained from Dharmacon (Lafayette, USA).

Several non-modified (siGENOME) siRNA's against Gpr12 were tested by bDNA assay (Quantiene bDNA assay kit, Bayer) in vitro using Neuro 2a cells. siRNA was designed using a multi component rational design algorithm (Reynolds et al., (2004). Nat Biotechnol 22, 326-330) and controlled for specificity towards Gpr12 by BLAST search.

The following siRNAs were chosen for further in vivo characterization:

```
Gpr12 siRNA2 sense strand
GAGGCACGCCCAUCAGAUAUU;                  SEQ ID NO: 7

Gpr12 siRNA2 anti-sense strand
UAUCUGAUGGGCGUGCCUCUU;                  SEQ ID NO: 8 non-targeting siRNA sense strand
UAGCGACUAAACACAUCAAUU;                  SEQ ID NO: 9 non-targeting siRNA antisense strand
UUGAUGUGUUUAGUCGCUAUU;                  SEQ ID NO: 10
```

Example 4

In Vivo Delivery of Synthetic Gpr12 siRNA in Mice

Animals and Environment. Young-adult (10-12 weeks old) C57BL/6 male mice (Taconic, N.Y.) were used. Upon arrival, mice were group-housed (5 mice) in standard laboratory cages and maintained on a 12:12 hours light-dark cycle. The experiments were always conducted during the light phase of the cycle. After surgery for cannulation, mice were single housed in individual cages and maintained so till the end of the experiment. With the exception of training and testing times, the mice had ad libitum access to food and water. Mice were maintained and bred under standard conditions, consistent with National Institutes of Health (NIH) guidelines and approved by the Institutional Animal Care and Use Committee.

Animal surgery and siRNA injection. For the injection of siRNA, mice were anesthetized with 20 mg/kg Avertin and implanted with a 33-gauge guide cannula bilaterally into the dorsal hippocampus (coordinates: A=−1.8 mm, L=+/−1.5 mm to a depth of 1.2 mm) or into amygdala (coordinates. A=−1.58 mm, L=+/−2.8 mm to a depth of 4.0 mm) (Franklin and Paxinos, 1997 *The Mouse Brain in Stereotaxic Coordinates*). Five to nine days after recovery from surgery, animals were injected with siRNA. siRNA was diluted to 0.5 μg per μl in 5% glucose and mixed with 6 equivalents of a 22 kDa linear polyethyleneimine (Fermentas). After 10 min of incubation at room temperature, 2 μl were injected into each hippocampus through an infusion cannula that was connected to a microsyringe by a polyethylene tube. The entire infusion procedure took ~2 min, and animals were handled gently to minimize stress. A total of 3 infusions of siRNA were given over a period of 3 days (1 μg siRNA per hippocampus per day).

siRNA mediated knockdown of Gpr12 may cause damage to the hippocampal formation. The hippocampal morphology of siRNA treated brains was evaluated.

siRNA injected animals were sacrificed one day after the behavioral experiments. Frozen brains were sliced into 15 μm sections and stained with Cresyl violet. Hippocampal morphology was evaluated on photographs of serial sections. For cannula verification, animals were injected with 1 μl of methyl blue dye and sacrificed immediately afterwards. Frozen brains were sliced into 15 μm sections. The position of the dye staining was determined microscopically and compared to (Franklin and Paxinos, 1997 *The Mouse Brain in Stereotaxic Coordinates*). Cannula verification was performed blind to the treatment of the subject.

Figure 6:
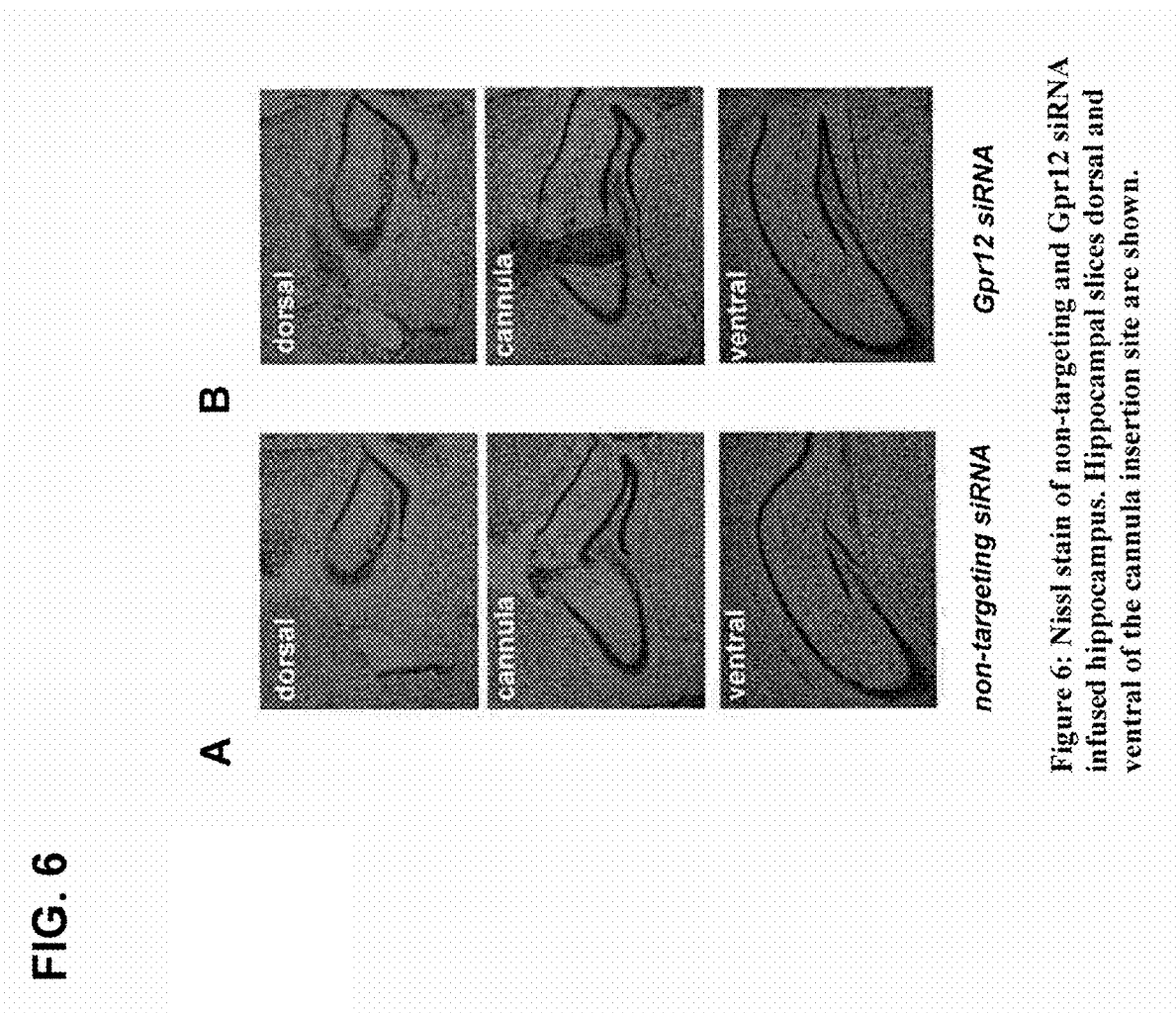
FIG. 6 is a picture of Niss1 stain of non-targeting (A) and Gpr12 siRNA (B) on infused hippocampus. Hippocampal slices of the dorsal and ventral of the cannula insertion site are shown.

There were no obvious differences in hippocampal morphology between non-targeting siRNA (FIG. 6a) and Gpr12 siRNA treated mice (FIG. 6b). Hence, Gpr12 siRNA did not cause any obvious changes in brain morphology. Damage to the pyramidal cell layer was restricted to the area of cannulation. Note that the damage visible in FIG. 6 (middle panel) is facilitated by the removal of the hippocampal cannula. It does not represent the actual surgery induced alterations in hippocampal morphology, which is considered to be minimal and does not affect behavioral performance of the experimental subjects.

Figure 7:
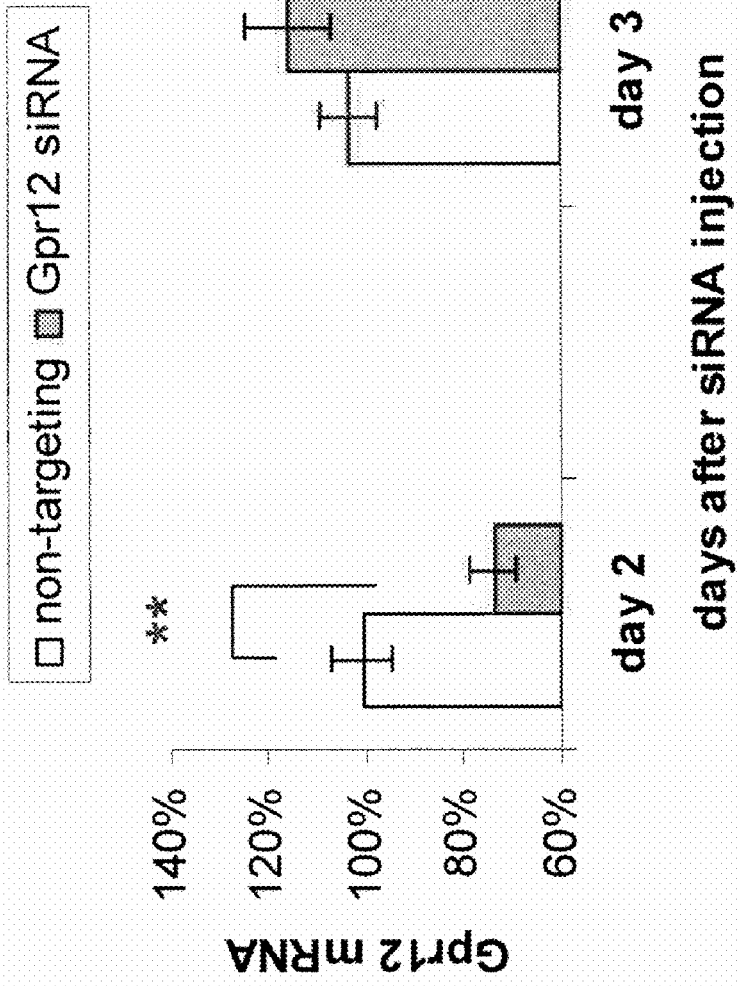
FIG. 7 is a bar graph of the hippocampal Gpr12 mRNA levels 2 and 3 days after Gpr12 siRNA treatment.

To confirm target knockdown by siRNA in vivo, mice were treated with intra-hippocampal siRNA for 3 days and determined Gpr12 mRNA levels at 2 and 3 days after the last siRNA infusion (FIG. 7).

For evaluation of Gpr12 knockdown in vivo, siRNA injected hippocampal tissue of 6 mice per group was pooled. 6 individual RNA preparations were performed using the QIAgen RNeasy kit (Qiagen) according to the manufacturer's specifications. cDNA was generated using TaqMan Reverse transcriptase kit (Applied Biosystems). 2 real-time PCR reactions per RNA-cDNA replication were performed using the ABI prism and SDS 2.1 software. ABI assays on demand (Applied Biosystems) were used to test the mRNA levels of Gpr12. The average CT value for each cDNA sample was determined. Data was then normalized to TATA binding protein (TBP) and ACT values were determined. mRNA levels were normalized to a non-targeting control siRNA treated control group.

When compared to non-targeting control siRNA (n=6), Gpr12 siRNA (n=6) significantly reduced hippocampal mRNA levels of Gpr12 at 2 days after treatment (p<0.01). There was no significant effect of Gpr12 siRNA at 3 days after treatment, indicating that the Gpr12 mRNA knockdown was transient (p=0.25). These results confirm that siRNA reduced Gpr12 mRNA in hippocampus in vivo. However, target mRNA and protein levels may be affected differentially by Gpr2 siRNA. The actual protein levels of Gpr12 may be reduced to a stronger degree and for a longer time-span following siRNA treatment.

Example 5

Effect of siRNA Mediated Knockdown of Gpr12 on Contextual and Trace Conditioning To assess contextual memory, a standardized contextual fear conditioning task originally developed for evaluation of memory in CREB knock-out mice ((Bourtchouladze et al., 1994 Cell 79, 59-68) was used. On the training day, the mouse was placed into the conditioning chamber (Med Associates, Inc., VA) for 2 minutes before the onset of the unconditioned stimulus (US), a 0.5 mA foot shock of 2 seconds duration. For weak training (2 training trials), the US was repeated two times with a 1 min inter-trial interval between shocks. For strong training (5 training trials), 5 foot shocks were given with a 1 min inter-trial interval between shocks (Bourtchouladze et al., 1998 Learn Mem 5, 365-374); (Scott et al., 2002 J Mol Neurosci 19, 171-177); (Tully et al., 2003 Nat Rev Drug Discov 2, 267-277). Training was performed using an automated software package (Med Associates, Inc., VA). After the last training trial, the mice were left in the conditioning chamber for another 30 sec and were then placed back in their home cages. Contextual memory was tested 24 hrs after training. The mouse was placed into the same training chamber and conditioning was assessed by scoring freezing behavior. Freezing was defined as the complete lack of movement in intervals of 5 seconds ((Fanselow and Bolles. 1979 J Comp Physiol Psychol 93, 736-744); (Bourtchouladze et al., 1994 Cell 79, 59-68); (Bourtchouladze et al., 1998 Learn Mem 5, 365-374). Total testing time lasted 3 minutes. After each experimental subject, the experimental apparatus was thoroughly cleaned with 75% ethanol, water, dried, and ventilated. Each experiment was filmed. All experimenters were blind to the drug and training conditions.

All behavioral experiments were designed and performed in a balanced fashion, meaning that (i) for each experimental condition an equal number of experimental and control mice was used; (ii) each experimental condition was replicated several times, and replicate days were added to generate final number of subjects. The proceeding of each session was filmed. In each experiment, the experimenter was unaware (blind) to the treatment of the subjects during training and testing. Data were analyzed by Student's unpaired t test using a software package (StatView 5.0.1; SAS Institute, Inc). Except where stated, all values in the text and figures are expressed as MEAN±SEM.

Figure 4:
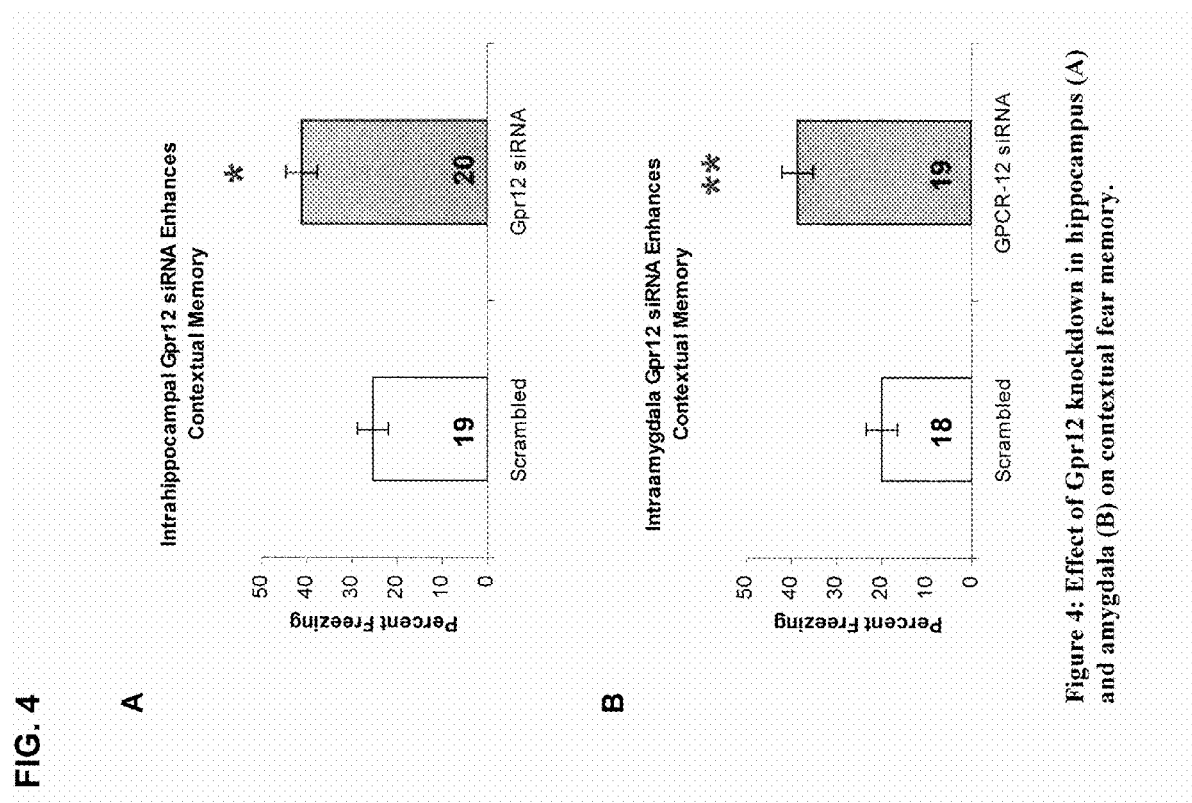
FIG. 4a is a bar graph of the effect of Gpr12 siRNA in mouse hippocampus on contextual memory.
FIG. 4b is a bar graph of the effect of Gpr12 siRNA in mouse amygdala on contextual memory.

The function of hippocampal Gpr12 in contextual memory was investigated first. Mice were infused with non-targeting (n=19) or Gpr12 siRNA (n=20) into the hippocampus. 3 days after the last siRNA infusion the animals were trained with a contextual conditioning paradigm designed to induce a weak contextual memory (Scott et al., 2002 J Mol Neurosci 19, 171-177) (Tully et al., 2003 Nat Rev Drug Discov 2, 267-277). Gpr12 DM-2 siRNA treated animals demonstrated significantly enhanced contextual memory at 24 h after training (24 h memory: $p<0.05$, FIG. 4a).

The function of Gpr12 in the amygdala for contextual memory formation was investigated next. Mice were infused with non-targeting (n=20) or Gpr12 siRNA (n=21) into the amygdala and tested in contextual memory. As for Gpr12 knockdown in hippocampus, Gpr12 siRNA treated animals demonstrated significantly enhanced contextual memory at 24 h after training (24 h memory: $p<0.01$, FIG. 4b). Four mice (2× non-targeting siRNA, 2×Gpr12-2 siRNA) were excluded from the analysis because of inaccurate cannula placements.

For trace conditioning training a standardized mouse contextual fear conditioning equipment (Med Associates, Inc., VA; (Bourtchouladze et al., 1994 Cell 79, 59-68); (Bourtchouladze et al., 1998 Learn Mem 5, 365-374) was used. On the training day, the mouse was placed into the conditioning chamber for 2 minutes before the onset of the conditioned stimulus (CS), a 2800 Hz tone, which lasted for 20 seconds at 75 dB. Sixty seconds after the end of the tone a 0.5 mA shock unconditioned stimulus (US) was delivered to the animal for two seconds. Previous experiments have revealed that this training paradigm induces poor trace fear memory in C57BL/6 mice, and that this memory can be facilitated by enhancers of the CREB pathway. After an additional 30 s in the chamber, the mouse was returned to its home cage. After each experimental subject, the experimental apparatus was thoroughly cleaned with 75% ethanol, water, dried, and ventilated for a few minutes.

Testing was done in a novel chamber located in another procedural room to avoid confounding effects of contextual conditioning. The internal conditioning chamber was removed and replaced with a mouse cage. Different colored tape was placed on the backside of each cage to differentiate one from another. Three different cages were used in rotation in order to decrease the possibility of scent contamination from subject to subject. A 30-watt lamp was placed inside the chamber to insure difference in illumination between training and testing. The cages were cleaned using a soapy solution instead of ethanol. Each test began with two minutes of light only (pre-CS), then 20 seconds of tone presentation (CS), followed by an additional 30 seconds of light only (post-CS). In the same manner as during training, the mice were scored one at a time for "freezing" in five-second intervals, as for contextual conditioning described above. The proceeding of each experiment was filmed. The proportion of the freezing response specific to the auditory memory was determined by subtraction of preCS freezing (non-specific) from CS freezing.

Figure 5:
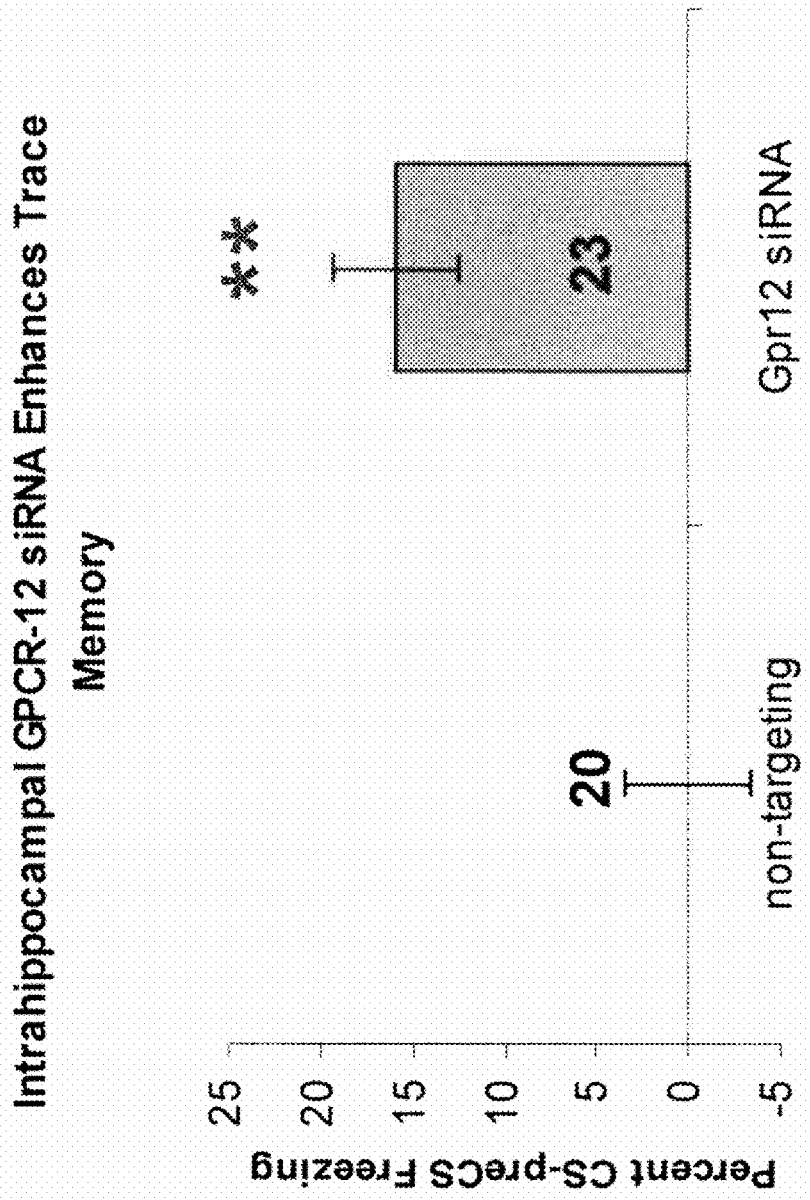
FIG. 5 is a bar graph of the effect of Gpr12 siRNA in mouse hippocampus on trace fear memory.

The function of hippocampal Gpr12 in trace fear memory was investigated. Mice were infused with non-targeting (n20) or Gpr12 siRNA (n=23) into hippocampus as described for contextual conditioning. When trained with one CS/US pairing and a 60 seconds trace interval, Gpr12 DM-2 siRNA treated animals demonstrated significantly increased trace conditioning (CS-preCS: $p<0.01$, FIG. 5). Importantly, Gpr12 siRNA, but not control siRNA, treated animals increased their freezing response upon tone CS presentation. Thus, similarly to contextual conditioning, siRNA-mediated knockdown of hippocampal Gpr12 facilitated trace conditioning. Gpr12 siRNA did not significantly affect immediate freezing during trace fear conditioning (non-targeting siRNA: 3.3±1.5%; Gpr12 siRNA: 5.1±1.6%; $p=0.44$; data not shown).

Taken together these results indicate that Gpr12 is a negative regulator of memory formation in both the hippocampus and the amygdala, two temporal lobe structures that are critical to memory formation in mice as well as in humans. Importantly, Gpr12 siRNA induced a 'gain of function' (that is, enhancement of memory formation). It is unlikely that this effect on behavioral plasticity is induced by side effects of Gpr12 siRNA. Thus, Gpr12 is a critical regulator of memory in hippocampus and amygdala.

Example 6

Gpr12 Knockout Mice

Gpr1 knockout mice. Gpr12 knockout mice were licensed from Deltagen (San Carlos, Calif. 94070, U.S.A). Heterozygous Gpr12 KO mice (referred to as Gpr12+/− mice) in predominantly C57Bl/6 background (five backcrosses into C57Bl/6) and WT littermate controls were generated by breeding male Gpr12+/− mice to C57Bl/6 females (Taconie Farms, USA). The mice were genotyped by polymerase chain reaction. Male and female mice balanced by gender were used at an age of 3-6 month for behavioral analysis.

Evaluation of Gpr12 and control mRNA levels in hippocampus of Gpr12+/− mice. Hippocampi were isolated from Gpr12+/− mice (n=3), Gpr12−/− mice (n=2) and WT littermate controls (n=3). RNA was isolated using the QIAgen RNeasy kit (Qiagen). cDNA was generated using TagMan Reverse Transcriptase kit (Applied Biosystems). mRNA levels of Gpr12, Creb1, and Grin1 were determined using ABI assay on Demand (Applied Biosystems) and normalized to TATA binding protein (TBP).

Novel Object Recognition Training and Testing. Animals were handled for 3-5 minutes for 3 days. The day before training, an individual animal was placed into a training apparatus (a Plexiglas box of L=48 cm; W=38 cm and H=20 cm) located in a dimly lit room and allowed to habituate to the environment for 15 minutes (see also Bourtchouladze, 2003). Training was initiated twenty-four hours after habituation. An animal was placed back into the training box, which contained two identical objects (e.g. a small conus-shaped object) and was allowed to explore these objects. The objects were placed into the central area of the box and the spatial position of objects (left-right sides) was counterbalanced between subjects. Animals were trained for 10, 15 or 20 minutes. Mice spending less than two seconds exploring were excluded from the analysis.

To test for long-term memory retention, mice were observed for 10 minutes 24 hours after training. To test for short-term (transcription-independent) memory, mice were observed for 10 minutes at 3 hours after training (Bourtchouladze, 2003). Animals were presented with two objects, one of which was used during training, and thus was 'familiar' and the other of which was novel (e.g., a small pyramid-shaped object). An object-memory index was determined as ((novel exploration−familiar exploration)/total exploration)*100. To control for non-specific effects on exploration the total time exploring during testing was also calculated.

To ensure that the discrimination targets do not differ in smell, after each experimental subject, the apparatus and the objects were thoroughly cleaned with 90% ethanol, dried and ventilated for a few minutes.

Open field. This is a commonly used test to measure motor activity and exploration of animals (Logue, 1997, Barad, 1998). The animals were moved from general animal housing to the laboratory 1 hour prior to the start of testing. The experiments were performed similarly to those described previously (Barad, 1998). Mice were placed in a standard open field and observed for 30 minutes using a computerized tracking system (EthoVision by Noldus, Inc., VA). Two boxes were run simultaneously and animals were scored for distance traveled (ambulation) and rearing. Between animals, the apparatus was thoroughly cleaned with 75% ethanol, dried, and ventilated for a few minutes. Experiments were performed by a blinded investigator and the proceedings of each experiment were videotaped. The following measures were quantified, 1) horizontal activity in the open field (ambulation), 2) vertical activity (rearing).

Table 3 shows results demonstrating the identification of Gpr12 as a memory regulated gene in hippocampus. P value and delta (log 2 of relative expression) are shown for Affymetrix gene-chip analysis. Trace conditioning data were independently confirmed by Nimble-chip analysis. Context conditioning data were confirmed by repetition of Affymetrix-chip and by qPCR.

TABLE 3

| Comparison | Time-point | P value (p < 0.05 for significance) | Delta (log2 value) | Confirmation |
|---|---|---|---|---|
| Trace conditioned vs. Naïve (caged) | 1 h | 0.033 | −0.14 | Nimble-chip |
| Context conditioned vs. Naïve (caged) | 1 h | 0.0003 | −0.28 | Affy-chip, qPCR |

Chronic inhibition of Gpr12 in heterozygous KO mice (Gpr12+/− mice). siRNA data indicates that long-term memory is facilitated by acute inhibition of Gpr12 in intact adult mice. To test the effect of chronic, system wide, inhibition of Gpr12 on long-term memory, Gpr12-mice were analyzed.

Homozygous Gpr12 knockout mice (Gpr12−/− mice) have previously been analyzed. Homozygous knockout mice exhibit impaired locomotion, impaired motor-performance on the Rotarod, impaired motor function and learning (swimming) in the Morris Water Maze, hyperanalgesia, and they show signs of liver and kidney disease (patent application WO 2005/027628, Carlton, 2005). An additional study demonstrated that homozygous Gpr12 knockout mice develop dyslipidemia and obesity (Bjursell, 2006). Overall, these findings have shown that homozygous Gpr12 knockout mice have a variety of general and developmentally induced health problems. It is expected that cognitive function is impaired in these mutants because of general ill-health.

While no data is available for heterozygous Gpr12 KO mice (Gpr12+/−) it is expected from these previous studies (Carlton, 2005; Bjursell, 2006) that long-term memory is impaired in these mice, although to a lesser degree than in homozygous mutants. However, an unanticipated outcome would be if long-term memory consolidation is enhanced in Gpr12+/− mice.

Figure 8:
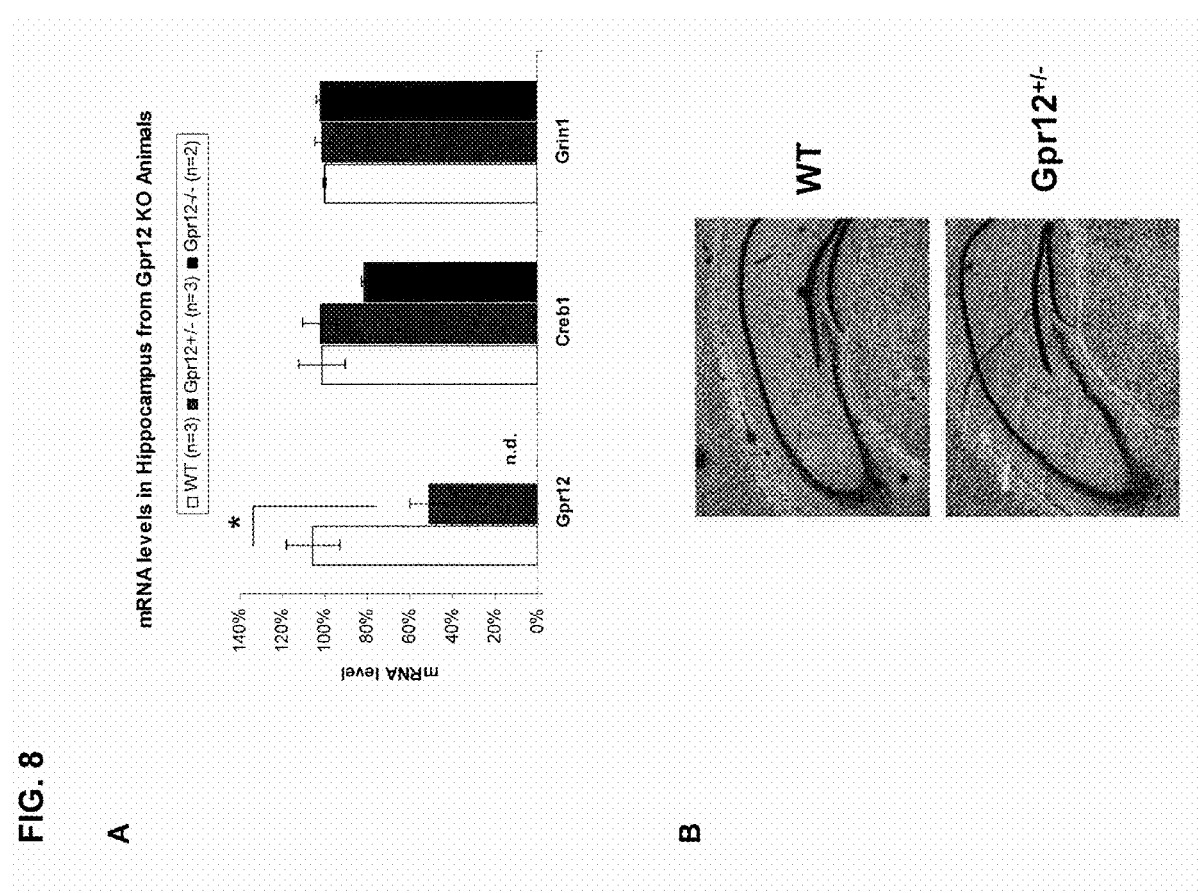
FIG. 8a shows qPCR analysis of Gpr12, Creb1, and Grin1 mRNA levels in Gpr12-/-. Gpr12+/- mice and WT control littermates. Gpr12 mRNA was reduced to 51% of control in Gpr12+/- mice and nonop-detectable in homozygous KO mice. In contrast, Creb1 and Grin1 mRNA was not affected.
FIG. 8b shows gross analysis of Gpr12+/- and WT hippocampal morphology (Cresyl violet stain). No obvious abnormalities were observed in Gpr+/- mice.

Both Gpr12 alleles are inactivated in Gpr12−/− mice and these mice have no detectable expression of Gpr12 mRNA (0% of WT controls), expression of Creb1 was slightly reduced while Grin1 levels were normal (81±1% and 102±2% of control, respectively; FIG. 8a).

Only one of two Gpr12 alleles is inactivated in Gpr12+/− mice, and these mice exhibit 51±8% of WT Gpr12 mRNA Gpr12 mRNA levels are thus distinct from homozygous knockout mice. mRNA of Creb1 and Grin1 was not affected in Gpr12+/− mice (102±8% and 101±4%, respectively; FIG. 8a). Gross histological analysis of Gpr12+/− hippocampus by Cresyl violet stain did not reveal any obvious differences between heterozygous mutants and WT controls (FIG. 8b).

General motor activity and open field exploration in heterozygous Gpr12 knockout mice. An open field test to examine if general motor activity and exploration are impaired in Gpr12+/− mice, as expected from previous results on homozygous KO mice was conducted. Horizontal activity (ambulation) in the open field was measured and found no difference in locomotor activity between heterozygous mutants and WT mice (p>0.05 for all time-points; student's t-test; FIG. 9a). There was also no difference in vertical activity (rearing) between Gpr12+/− mice and WT controls (p>0.05 for all time-points; student's t-test; FIG. 9b). These results indicate that motor activity and exploration are normal in heterozygous Gpr12 mutant mice.

Novel Object Recognition memory in heterozygous Gpr12 knockout mice. Object recognition is an ethnologically relevant task for mice and rats, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than a familiar one. Recent neuroimaging studies in humans demonstrated that memory in object recognition involves the prefrontal cortex (Deibert, 1999), a structure that is strongly affected by aging (Hedden, 2004). Other studies on monkeys and rodents suggest that the hippocampus is important for novel object recognition (Teng, 2000; Mumby, 2001). Hence, novel object recognition provides a good behavioral model to evaluate drug-compound effects on cognitive tasks associated with unction of the hippocampus and cortex in experimental animals.

Figure 10:
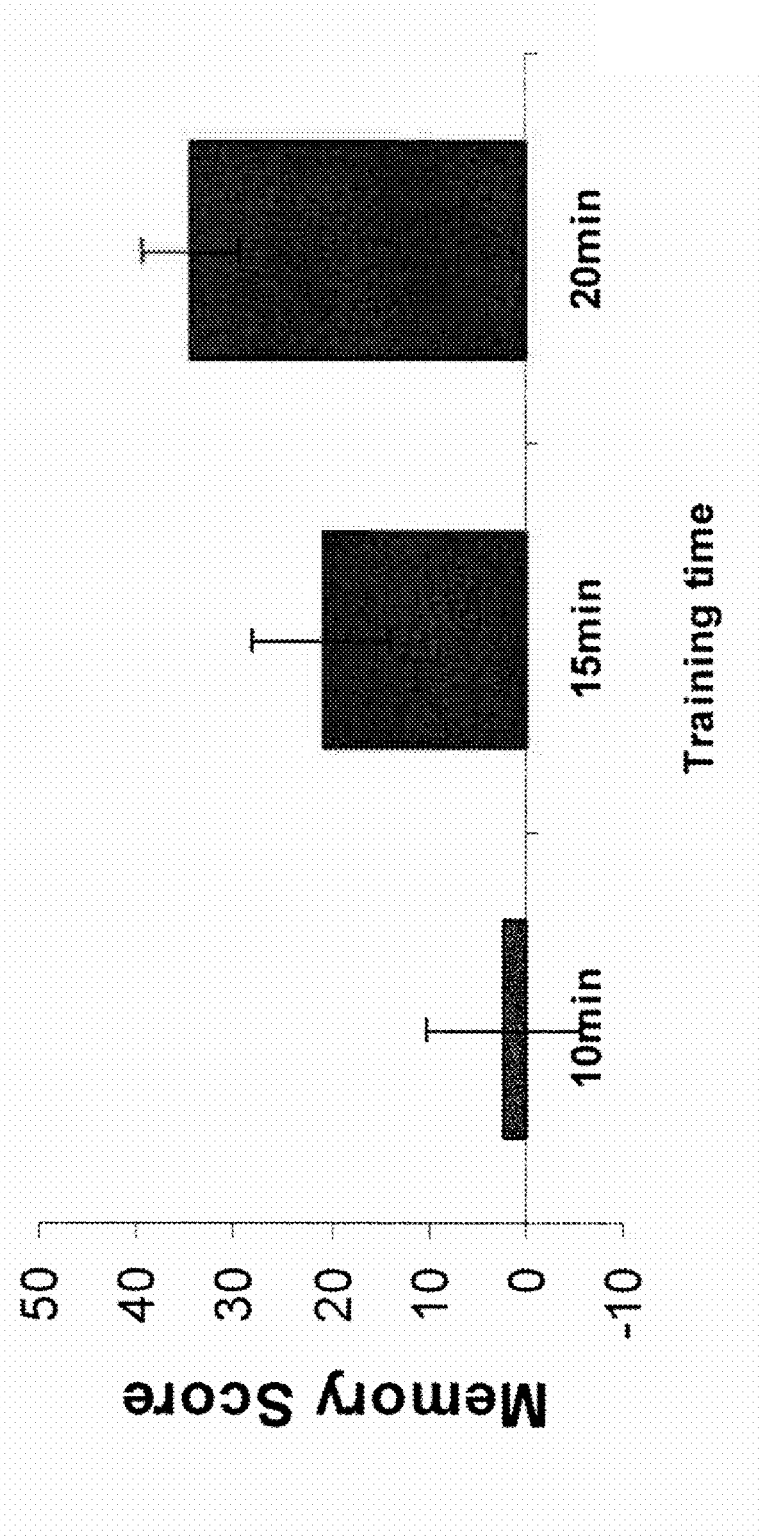
FIG. 10 shows NOR memory in WT mice (n=19) as long-term retention of object recognition memory is dependent on training time.

As for contextual and trace conditioning, long-term memory for object recognition is dependent on the training conditions (Bourtchouladze, 2003). To establish conditions that permit short-term but not long-term retention of memory for object recognition training WT mice (n=19) of the same genetic background as the Gpr12 mutants were trained for 10 min, 15 min, or min (FIG. 10). When tested 24 hours later: mice trained for 10 min showed no preference for the novel object (memory score: 2.2±8.0), whereas mice trailed for 15 min or 20 min demonstrated a preference for the novel object (memory score: 21.0±7.0 and 34.3±4.9, for 15 min and 20 min training, respectively). Thus, 10 min of training were not sufficient to induce long-term object recognition memory.

Next, long-term object recognition memory in Gpr12+/− (n=15) and WT littermates (n=16) after 10 min training (FIG. 11) was tested. When tested after 24 hours Gpr12+/− mice, but not WT controls, demonstrated long-term object recognition memory (memory score: 6.0±8.2 vs. 28.7±4.9 for WT vs. Gpr12+/− mice, respectively, p<0.05, student's unpaired t-test; FIG. 11a). There was no difference in total exploration during training (p=0.34) and testing (p=0.63), indicating that facilitation of long-term memory in Gpr12+/− mice was not due to a general increase in exploratory activity (FIG. 11b).

Short-term object recognition memory in Gpr12+/− (n=6) and WT littermates (n=8) (FIG. 12) was also conducted. Short-term object recognition memory was similar between mutants and controls when tested 3 hours after training (memory score: 25.6±6.6 vs. 18.2±4.8 for WT vs. Gpr12+/− mice, respectively; p=0.41, student's unpaired t-test; FIG. 12a). There was no difference between the groups in total exploration during testing (p=0.28; FIG. 12b). Importantly and consistent with previous studies (Bourtchouladze, 2003), WT mice demonstrated significant short-term retention of object memory after 10 min training. However, only Gpr12+/− mice showed long-term retention (FIG. 11), indicating that heterozygous knockdown of Gpr12 specifically enhances long-term memory.

Accordingly, heterozygous Gpr12 mutant mice (harboring one functional Gpr12 allele) have no obvious deficits in motor activity and exploration. Analysis of long-term object recognition memory revealed the unanticipated finding that long-term memory consolidation is enhanced in heterozygous Gpr12 knockout mice. Short-term memory, in contrast, was normal. These findings are consistent with facilitation of contextual and temporal memory after siRNA inhibition of Gpr12 in hippocampus and amygdala.

All publications, patent and patent applications mentioned in this specification used herein to illuminate the background of the invention, and in particular, cases to provide additional details respecting the practice are incorporated herein by reference to the same extent as if each individual publication, patent or patent application was specifically and individually incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising the steps of:
   (a) administering to a mammal an effective amount of a pharmaceutical agent which inhibits Gpr12 activity in the mammal;
   (b) providing training to the mammal under conditions sufficient to produce an improvement in performance by the mammal of a cognitive task;
   (c) producing a long-lasting performance gain in the mammal relative to the performance of said cognitive task achieved by training alone;
   wherein said pharmaceutical agent comprises an effective amount of a Gpr12 siRNA molecule or an effective amount of a biologically active Gpr12 antisense fragment.

2. The method of claim 1 wherein the mammal is an adult mammal.

3. The method of claim 1 wherein the mammal is a human.

4. The method of claim 1, wherein said administering results in enhancement in long term memory formation.

5. The method of claim 4, wherein the mammal shows normal short-term memory relative to animals that have not been administered the pharmaceutical agent.

6. The method of claim 4, further comprising detecting said enhancement in said long term memory formation.

7. The method of claim 6 wherein said detecting of said enhancement is the detection of enhancement of a hippocampal-dependent cognitive task.

8. The method of claim 6 wherein said detecting of said enhancement is the detection of enhancement of an amygdala-dependent cognitive task.

9. The method of claim 6 wherein said detecting of said enhancement is the detection of enhancement of a hippocampal-dependent cognitive task and an amygdala-dependent cognitive task.

10. The method of claim 1 wherein the inhibition of Gpr12 activity comprises inhibition of Gpr12 protein expression in the mammal.

11. The method of claim 1 wherein the training comprises multiple training sessions.

12. The method of claim 1 wherein the training comprises spaced training sessions.

13. The method of claim 11 wherein said pharmaceutical agent is administered before and/or during each training session.

14. A method comprising the steps of
   (a) introducing a pharmaceutical agent of interest into host cells expressing a Gpr12 protein; and
   (b) determining Gpr12 function, wherein a decrease in the Gpr12 function determined in (b) compared to the Gpr12 function of host cells of step (a) to which said pharmaceutical agent has not been administered identifies the pharmaceutical agent as a candidate drug capable of inhibiting Gpr12 function;
   (c) administering to a mammal the candidate drug identified in step (b);

(d) training said mammal of step (c) and a control mammal of the same species to which the candidate drug has not been administered under conditions sufficient to produce long term memory formation;

(e) assessing long term memory formation in said mammals, trained in step (d); and (f) comparing long term memory formation in said mammals assessed in step (e), wherein an increase in long term memory formation assessed in said mammal administered the pharmaceutical agent relative to long term memory formation assessed in said control mammal identifies the candidate drug as one capable of enhancing long term memory formation.

15. The method of claim 14 wherein said mammals are adult mammals.

16. The method of claim 14 wherein said mammals are humans.

17. The method of claim 14 wherein said long term memory formation is hippocampus-dependent long term memory formation.

18. The method of claim 14 wherein said long term memory formation is amygdala-dependent long term memory formation.

19. The method of claim 14 wherein said long term memory formation is hippocampus-dependent and amygdala-dependent long term memory formation.

20. The method of claim 14 wherein the inhibition of Gpr12 activity comprises inhibition of Gpr12 protein expression in the mammal.

21. The method of claim 14 wherein the training comprises multiple training sessions.

22. The method of claim 14 wherein the training comprises spaced training sessions.

23. The method of claim 14 wherein said pharmaceutical agent is administered before and/or during each training session.

24. The method of claim 14 wherein said pharmaceutical agent comprises an effective amount of a Gpr12 siRNA molecule or an effective amount of a biologically active Gpr12 antisense fragment.

* * * * *

SEQUENCE LISTING

<160> NUMBER OF SEQ ID NOS: 10

<210> SEQ ID NO 1
<211> LENGTH: 334
<212> TYPE: PRT
<213> ORGANISM: Mus musculus

<400> SEQUENCE: 1

Met Asn Glu Asp Pro Lys Val Asn Leu Ser Gly Leu Pro Arg Asp Cys
1               5                   10                  15

Ile Asp Ala Gly Ala Pro Glu Asn Ile Ser Ala Ala Val Pro Ser Gln
            20                  25                  30

Gly Ser Val Ala Glu Ser Glu Pro Glu Leu Val Val Asn Pro Trp Asp
        35                  40                  45

Ile Val Leu Cys Ser Ser Gly Thr Leu Ile Cys Cys Glu Asn Ala Val
    50                  55                  60

Val Val Leu Ile Ile Phe His Ser Pro Ser Leu Arg Ala Pro Met Phe
65                  70                  75                  80

Leu Leu Ile Gly Ser Leu Ala Leu Ala Asp Leu Leu Ala Gly Leu Gly
                85                  90                  95

Leu Ile Ile Asn Phe Val Phe Ala Tyr Leu Leu Gln Ser Glu Ala Thr
            100                 105                 110

Lys Leu Val Thr Ile Gly Leu Ile Val Ala Ser Phe Ser Ala Ser Val
        115                 120                 125

Cys Ser Leu Leu Ala Ile Thr Val Asp Arg Tyr Leu Ser Leu Tyr Tyr
    130                 135                 140

Ala Leu Thr Tyr His Ser Glu Arg Thr Val Thr Phe Thr Tyr Val Met

```
           145                 150                 155                 160
Leu Val Met Leu Trp Gly Thr Ser Ile Cys Leu Gly Leu Leu Pro Val
                    165                 170                 175
Met Gly Trp Asn Cys Leu Arg Asp Glu Ser Thr Cys Ser Val Val Arg
                180                 185                 190
Pro Leu Thr Lys Asn Asn Ala Ala Ile Leu Ser Ile Ser Phe Leu Phe
            195                 200                 205
Met Phe Ala Leu Met Leu Gln Leu Tyr Ile Gln Ile Cys Lys Ile Val
        210                 215                 220
Met Arg His Ala His Gln Ile Ala Leu Gln His His Phe Leu Ala Thr
225                 230                 235                 240
Ser His Tyr Val Thr Thr Arg Lys Gly Val Ser Thr Leu Ala Leu Ile
                    245                 250                 255
Leu Gly Thr Phe Ala Ala Cys Trp Met Pro Phe Thr Leu Tyr Ser Leu
                260                 265                 270
Ile Ala Asp Tyr Thr Tyr Pro Ser Ile Tyr Thr Tyr Ala Thr Leu Leu
            275                 280                 285
Pro Ala Thr Tyr Asn Ser Ile Ile Asn Pro Val Ile Tyr Ala Phe Arg
        290                 295                 300
Asn Gln Glu Ile Gln Lys Ala Leu Cys Leu Ile Cys Cys Gly Cys Ile
305                 310                 315                 320
Pro Ser Ser Leu Ser Gln Arg Ala Arg Ser Pro Ser Asp Val
                    325                 330

<210> SEQ ID NO 2
<211> LENGTH: 2485
<212> TYPE: DNA
<213> ORGANISM: Mus musculus

<400> SEQUENCE: 2
aagggaacaa taatttgcag accggccaac tgcaatctaa gagagggagt cgcttgctgt      60
tgtaagtctc ctccgccagc cctaacctgc ttaccccgca ttcctcctgt tcatcccgaa     120
aacccggccg tttacaattc tttaggggaa agcataagaa gccgagcccc agggtcaagg     180
gcgcctcggg aagccacag  gatcaaagta ggtcgccaga ctctccggcc gttcgagtgg     240
gtcttcgcat gactgttgca ggcgggcgtc cacggtggcg ggctcccgcc cctcacgcag     300
ctgcgacctg cggggcgcg  cgcagcctcg tggggttccc gcggatgcgc gcccggcggg     360
gagcgcggag ggcggagagc cgggcgcgag caccgcagct cacctgccgc gggcgccacc     420
acggacgtgc cacgcgggtg gcccgagcta ttcggcagca ctgaaggagc cacccctcgg     480
ccagggcgtg ccaaggacag gggttaaaat gaacgaagac ccgaaggtca atttaagcgg     540
gctgcctcgg gactgtatag atgccggtgc tccagagaac atctcagccg ctgtcccctc     600
ccagggctct gttgcggagt cagaacccga gctcgttgtc aaccctggg  acattgtctt     660 gtgcagctca ggaaccctca tctgctgtga aaatgccgtt gtggtcctta tcatcttcca     720
cagccccagc ctgcgagccc ccatgttcct actgataggc agcctggctc ttgcagacct     780
gctggctggc ctgggactca tcatcaattt tgttttttgcg tacctgcttc agtcagaagc     840
caccaagctg gtcaccatcg gactcattgt cgcctctttc tctgcctctg tctgcagttt     900
gctggctatt actgtggacc gctacctctc gctatattac gccctgacgt accactccga     960
gaggaccgtc acctttacct atgtcatgct agtgatgctc tggggaacct ccatctgcct    1020
ggggctgctg cccgtcatgg gctggaactg cttgagggac gagtccacct gcagcgtggt    1080
cagacctctc actaagaaca acgctgccat cctctccatc tccttcctct tcatgtttgc    1140
```

| | |
|---|---|
| tctgatgctt cagctctaca tccagatttg taagattgtg atgaggcacg cccatcagat | 1200 |
| agccctgcag caccacttcc tggctacatc gcactatgtg actacccgga aagggtctc | 1260 |
| gaccctggct ctcatcctag ggacctttgc tgcctgctgg atgcctttca ccctctattc | 1320 |
| cttgatcgcc gattacacct acccttcgat ctatacctat gccaccctcc tgcccgccac | 1380 |
| ctacaattcc atcatcaacc tgtcattta cgctttcaga aaccaagaga tccagaaagc | 1440 |
| cctctgcctc atttgctgtg ggtgcatccc ttcctcgctg tctcagagag ctcggtctcc | 1500 |
| cagcgatgtg tagcagcctt ctcctcatag gacgctgcct ctaccaagcg ctcccacctc | 1560 |
| ccagggcggc cagtgatttc cttccttaaa ttctttgcac tggatctcac aagcagaagc | 1620 |
| aatgacatct tttagacacg tattgacagt ggaaatcatc ttaccagtgt tttttaaaaa | 1680 |
| aaaaacaaaa caaaactcga cttctcggct cagcattctg ttgtttggtt tgggagttag | 1740 |
| gatttgtttg tttgtttgct tgtttgtttg tttggagggt gtaatgggac ctcatgtggc | 1800 |
| catgaaatta tacaaaagtc tcggattttt ttaacctagg cttgaaaata aatcaaagtt | 1860 |
| ttaaaggaaa ctggagaagg aaatactttt tctgaaggaa atactttttt ttttttaatc | 1920 |
| aaggtagatc ttccattctg tatgtatcta acaggatagg agctttgcca tataaccaaa | 1980 |
| atagtttata taattacatt tggaagggct tgtgtttatt tctaggaatt cagtaataag | 2040 |
| tgaccagtaa cagaggcgcg aactcctttc tttcctttca gcagtagtga ctgctcttaa | 2100 |
| gaatcacttt gcagtttctc tgtgttacag tttggtatgc atggttacct gtggtagtca | 2160 |
| gatcactaat tgcaatattg ccatgttaaa cccagaatta aaagagtcat tttttcttca | 2220 |
| atacagtttt tgaaatatcc tttccaaagt gagtcatgaa aaaaatgttt ccaattacat | 2280 |
| atgagatagc actggttaga tttgtcattg tgatttttaa aactctagac tggtggtttt | 2340 |
| cagaaaacaa aagagaaaat attaacagca tctattgaaa gaagattta tttattttta | 2400 |
| atatattctg agagaataaa tggtgtgata ctattaagaa atatacaaac atgacttttc | 2460 |
| aaatctctaa aaaaaaaaaa aaaaa | 2485 |

<210> SEQ ID NO 3
<211> LENGTH: 2271
<212> TYPE: DNA
<213> ORGANISM: Mus musculus

<400> SEQUENCE: 3

| | |
|---|---|
| cggcatggga gatgcaatta gccaatgtcg gttttcagcg ttttggcaag tgtgcgagtg | 60 |
| tgcatgtgcc gcctcgggag tcctgatccg tgtttccctc agagacaaac agcatttcgg | 120 |
| ttgcagactt tagcttttgt ttttaattcc tgaagctcgt ggcattttga cactgatagc | 180 |
| tgagcccagg gttgtctgtc tttctctgtg tgttttgcat gatcttggat tggcacccta | 240 |
| ctgtacccaa acattaaaaa gcctgtcttt ccgttgaaga ggacagggt taaaatgaac | 300 |
| gaagacccga aggtcaattt aagcgggctg cctcgggact gtatagatgc cggtgctcca | 360 |
| gagaacatct cagccgctgt cccctcccag ggctctgttg cggagtcaga acccgagctc | 420 |
| gttgtcaacc cctgggacat tgtcttgtgc agctcaggaa ccctcatctg ctgtgaaaat | 480 |
| gccgttgtgg tccttatcat cttccacagc cccagcctgc gagccccat gttcctactg | 540 |
| ataggcagcc tggctcttgc agacctgctg gctggcctgg gactcatcat caattttgtt | 600 |
| tttgcgtacc tgcttcagtc agaagccacc aagctggtca ccatcggact cattgtcgcc | 660 |
| tcttctctg cctctgtctg cagtttgctg gctattactg tggaccgcta cctctcgcta | 720 |
| tattacgccc tgacgtacca ctccgagagg accgtcacct ttacctatgt catgctagtg | 780 |

-continued

```
atgctctggg gaacctccat ctgcctgggg ctgctgcccg tcatgggctg gaactgcttg      840
agggacgagt ccacctgcag cgtggtcaga cctctcacta agaacaacgc tgccatcctc      900
tccatctcct tcctcttcat gtttgctctg atgcttcagc tctacatcca gatttgtaag      960
attgtgatga ggcacgccca tcagatagcc ctgcagcacc acttcctggc tacatcgcac     1020
tatgtgacta cccggaaagg ggtctcgacc ctggctctca tcctagggac ctttgctgcc     1080
tgctggatgc ctttcaccct ctattccttg atcgccgatt acacctaccc ttcgatctat     1140
acctatgcca ccctcctgcc cgccacctac aattccatca tcaaccctgt catttacgct     1200
ttcagaaacc aagagatcca gaaagccctc tgcctcattt gctgtgggtg catcccttcc     1260
tcgctgtctc agagagctcg gtctcccagc gatgtgtagc agccttctcc tcataggacg     1320
ctgcctctac caagcgctcc cacctcccag ggcggccagt gatttccttc cttaaattct     1380
ttgcactgga tctcacaagc agaagcaatg acatctttta gacacgtatt gacagtggaa     1440
atcatcttac cagtgttttt taaaaaaaaa acaaaacaaa actcgacttc tcggctcagc     1500
attctgttgt ttggtttggg agttaggatt tgtttgtttg tttgcttgtt tgtttgtttg     1560
gagggtgtaa tgggacctca tgtggccatg aaattataca aaagtctcgg gattttttaa     1620
cctaggcttg aaataaaatc aaagttttaa aggaaactgg agaaggaaat acttttctg      1680
aaggaaatac tttttttttt ttaatcaagg tagatcttcc attctgtatg tatctaacag     1740
gataggagct ttgccatata accaaaatag tttatataat tacatttgga agggcttgtg     1800
tttatttcta ggaattcagt aataagtgac cagtaacaga ggcgcgaact cctttctttc     1860
ctttcagcag tagtgactgc tcttaagaat cactttgcag tttctctgtg ttacagtttg     1920
gtatgcatgg ttacctgtgg tagtcagatc actaattgca atattgccat gttaaaccca     1980
gaattaaaag agtcattttt tcttcaatac agttttttgaa atatcctttc caaagtgagt     2040
catgaaaaaa atgtttccaa ttacatatga gatagcactg gttagatttg tcattgtgat     2100
ttttaaaact ctagactggt ggttttcaga aaacaaaaga gaaaatatta acagcatcta     2160
ttgaaagaag attttatttta tttttaatat attctgagag aataaatggt gtgatactat     2220
taagaaatat acaaacatga cttttcaaat ctctaaaaaa aaaaaaaaaa a              2271
```

<210> SEQ ID NO 4
<211> LENGTH: 334
<212> TYPE: PRT
<213> ORGANISM: Mus musculus

<400> SEQUENCE: 4

```
Met Asn Glu Asp Pro Lys Val Asn Leu Ser Gly Leu Pro Arg Asp Cys
1               5                   10                  15

Ile Asp Ala Gly Ala Pro Glu Asn Ile Ser Ala Ala Val Pro Ser Gln
            20                  25                  30

Gly Ser Val Ala Glu Ser Glu Pro Glu Leu Val Val Asn Pro Trp Asp
        35                  40                  45

Ile Val Leu Cys Ser Ser Gly Thr Leu Ile Cys Cys Glu Asn Ala Val
    50                  55                  60

Val Val Leu Ile Ile Phe His Ser Pro Ser Leu Arg Ala Pro Met Phe
65                  70                  75                  80

Leu Leu Ile Gly Ser Leu Ala Leu Ala Asp Leu Ala Gly Leu Gly
                85                  90                  95

Leu Ile Ile Asn Phe Val Phe Ala Tyr Leu Leu Gln Ser Glu Ala Thr
            100                 105                 110
```

```
Lys Leu Val Thr Ile Gly Leu Ile Val Ala Ser Phe Ser Ala Ser Val
        115                 120                 125
Cys Ser Leu Leu Ala Ile Thr Val Asp Arg Tyr Leu Ser Leu Tyr Tyr
130                 135                 140
Ala Leu Thr Tyr His Ser Glu Arg Thr Val Thr Phe Thr Tyr Val Met
145                 150                 155                 160
Leu Val Met Leu Trp Gly Thr Ser Ile Cys Leu Gly Leu Leu Pro Val
                165                 170                 175
Met Gly Trp Asn Cys Leu Arg Asp Glu Ser Thr Cys Ser Val Val Arg
            180                 185                 190
Pro Leu Thr Lys Asn Asn Ala Ala Ile Leu Ser Ile Ser Phe Leu Phe
        195                 200                 205
Met Phe Ala Leu Met Leu Gln Leu Tyr Ile Gln Ile Cys Lys Ile Val
    210                 215                 220
Met Arg His Ala His Gln Ile Ala Leu Gln His His Phe Leu Ala Thr
225                 230                 235                 240
Ser His Tyr Val Thr Thr Arg Lys Gly Val Ser Thr Leu Ala Leu Ile
                245                 250                 255
Leu Gly Thr Phe Ala Ala Cys Trp Met Pro Phe Thr Leu Tyr Ser Leu
            260                 265                 270
Ile Ala Asp Tyr Thr Tyr Pro Ser Ile Tyr Thr Tyr Ala Thr Leu Leu
        275                 280                 285
Pro Ala Thr Tyr Asn Ser Ile Ile Asn Pro Val Ile Tyr Ala Phe Arg
    290                 295                 300
Asn Gln Glu Ile Gln Lys Ala Leu Cys Leu Ile Cys Cys Gly Cys Ile
305                 310                 315                 320
Pro Ser Ser Leu Ser Gln Arg Ala Arg Ser Pro Ser Asp Val
                325                 330

<210> SEQ ID NO 5
<211> LENGTH: 1005
<212> TYPE: DNA
<213> ORGANISM: Homo sapiens

<400> SEQUENCE: 5
atgaatgaag acctgaaggt caatttaagc gggctgcctc gggattattt agatgccgct      60
gctgcggaga acatctcggc tgctgtctcc tcccggggttc ctgccgtaga gccagagcct     120
gagctcgtag tcaaccccctg gacattgtc ttgtgtacct cgggaaccct catctcctgt      180
gaaaatgcca ttgtggtcct tatcatcttc cacaacccca gcctgcgagc acccatgttc     240
ctgctaatag gcagcctggc tcttgcagac tgctggccg gcattggact catcaccaat      300
tttgttttg cctacctgct tcagtcagaa gccaccaagc tggtcacgat cggcctcatt      360
gtcgcctctt tctctgcctc tgtctgcagc ttgctggcta tcactgttga ccgctacctc      420
tcactgtact acgctctgac gtaccattcg gagaggacgg tcacgtttac ctatgtcatg     480
ctcgtcatgc tctgggggac ctccatctgc ctggggctgc tgcccgtcat gggctggaac     540
tgcctccgag acgagtccac ctgcagcgtg gtcagaccgc tcaccaagaa caacgcggcc     600
atcctctcgg tgtccttcct cttcatgttt gcgctcatgc ttcagctcta catccagatc     660
tgtaagattg tgatgaggca cgcccatcag atagccctgc agcaccactt cctgccacg     720
tcgcactatg tgaccacccg gaaggggtc tccaccctgg ctatcatcct ggggacgttt      780
gctgcttgct ggatgccttt cacctctat tccttgatag cggattacac ctacccctcc     840
atctatacct acgccaccct cctgcccgcc acctacaatt ccatcatcaa ccctgtcata     900
```

```
tatgctttca gaaaccaaga gatccagaaa gcgctctgtc tcatttgctg cggctgcatc        960
ccgtccagtc tcgcccagag agcgcgctcg cccagtgatg tgtag                       1005
```

<210> SEQ ID NO 6
<211> LENGTH: 334
<212> TYPE: PRT
<213> ORGANISM: Homo sapiens

<400> SEQUENCE: 6

| | | | | | | | | | | | | | | |
|---|---|---|---|---|---|---|---|---|---|---|---|---|---|---|
| Met | Asn | Glu | Asp | Leu | Lys | Val | Asn | Leu | Ser | Gly | Leu | Pro | Arg | Asp | Tyr |
| 1 | | | | 5 | | | | | 10 | | | | | 15 | |
| Leu | Asp | Ala | Ala | Ala | Glu | Asn | Ile | Ser | Ala | Ala | Val | Ser | Ser | Arg | |
| | | 20 | | | | 25 | | | | 30 | | | | | |
| Val | Pro | Ala | Val | Glu | Pro | Glu | Pro | Glu | Leu | Val | Val | Asn | Pro | Trp | Asp |
| | | 35 | | | | 40 | | | | 45 | | | | | |
| Ile | Val | Leu | Cys | Thr | Ser | Gly | Thr | Leu | Ile | Ser | Cys | Glu | Asn | Ala | Ile |
| | 50 | | | | | 55 | | | | | 60 | | | | |
| Val | Val | Leu | Ile | Ile | Phe | His | Asn | Pro | Ser | Leu | Arg | Ala | Pro | Met | Phe |
| 65 | | | | | 70 | | | | | 75 | | | | | 80 |
| Leu | Leu | Ile | Gly | Ser | Leu | Ala | Leu | Ala | Asp | Leu | Leu | Ala | Gly | Ile | Gly |
| | | | | 85 | | | | | 90 | | | | | 95 | |
| Leu | Ile | Thr | Asn | Phe | Val | Phe | Ala | Tyr | Leu | Leu | Gln | Ser | Glu | Ala | Thr |
| | | | 100 | | | | | 105 | | | | | 110 | | |
| Lys | Leu | Val | Thr | Ile | Gly | Leu | Ile | Val | Ala | Ser | Phe | Ser | Ala | Ser | Val |
| | | | 115 | | | | | 120 | | | | | 125 | | |
| Cys | Ser | Leu | Leu | Ala | Ile | Thr | Val | Asp | Arg | Tyr | Leu | Ser | Leu | Tyr | Tyr |
| 130 | | | | | | 135 | | | | | 140 | | | | |
| Ala | Leu | Thr | Tyr | His | Ser | Glu | Arg | Thr | Val | Thr | Phe | Thr | Tyr | Val | Met |
| 145 | | | | | 150 | | | | | 155 | | | | | 160 |
| Leu | Val | Met | Leu | Trp | Gly | Thr | Ser | Ile | Cys | Leu | Gly | Leu | Leu | Pro | Val |
| | | | | 165 | | | | | 170 | | | | | 175 | |
| Met | Gly | Trp | Asn | Cys | Leu | Arg | Asp | Glu | Ser | Thr | Cys | Ser | Val | Val | Arg |
| | | | 180 | | | | | 185 | | | | | 190 | | |
| Pro | Leu | Thr | Lys | Asn | Asn | Ala | Ala | Ile | Leu | Ser | Val | Ser | Phe | Leu | Phe |
| | | | 195 | | | | | 200 | | | | | 205 | | |
| Met | Phe | Ala | Leu | Met | Leu | Gln | Leu | Tyr | Ile | Gln | Ile | Cys | Lys | Ile | Val |
| | 210 | | | | | 215 | | | | | 220 | | | | |
| Met | Arg | His | Ala | His | Gln | Ile | Ala | Leu | Gln | His | His | Phe | Leu | Ala | Thr |
| 225 | | | | | 230 | | | | | 235 | | | | | 240 |
| Ser | His | Tyr | Val | Thr | Thr | Arg | Lys | Gly | Val | Ser | Thr | Leu | Ala | Ile | Ile |
| | | | | 245 | | | | | 250 | | | | | 255 | |
| Leu | Gly | Thr | Phe | Ala | Ala | Cys | Trp | Met | Pro | Phe | Thr | Leu | Tyr | Ser | Leu |
| | | | 260 | | | | | 265 | | | | | 270 | | |
| Ile | Ala | Asp | Tyr | Thr | Tyr | Pro | Ser | Ile | Tyr | Thr | Tyr | Ala | Thr | Leu | Leu |
| | | 275 | | | | | 280 | | | | | 285 | | | |
| Pro | Ala | Thr | Tyr | Asn | Ser | Ile | Ile | Asn | Pro | Val | Ile | Tyr | Ala | Phe | Arg |
| | | 290 | | | | | 295 | | | | | 300 | | | |
| Asn | Gln | Glu | Ile | Gln | Lys | Ala | Leu | Cys | Leu | Ile | Cys | Cys | Gly | Cys | Ile |
| 305 | | | | | 310 | | | | | 315 | | | | | 320 |
| Pro | Ser | Ser | Leu | Ala | Gln | Arg | Ala | Arg | Ser | Pro | Ser | Asp | Val | | |
| | | | | 325 | | | | | 330 | | | | | | |

<210> SEQ ID NO 7
<211> LENGTH: 21
<212> TYPE: RNA
<213> ORGANISM: Artificial Sequence

```
<220> FEATURE:
<223> OTHER INFORMATION: Gpr12 siRNA2 sense strand

<400> SEQUENCE: 7
gaggcacgcc caucagauau u                                              21

<210> SEQ ID NO 8
<211> LENGTH: 21
<212> TYPE: RNA
<213> ORGANISM: Artificial Sequence
<220> FEATURE:
<223> OTHER INFORMATION: Gpr12 siRNA2  anti-sense strand

<400> SEQUENCE: 8
uaucugaugg gcgugccucu u                                              21

<210> SEQ ID NO 9
<211> LENGTH: 21
<212> TYPE: RNA
<213> ORGANISM: Artificial Sequence
<220> FEATURE:
<223> OTHER INFORMATION: non-targeting siRNA sense strand

<400> SEQUENCE: 9
uagcgacuaa acacaucaau u                                              21

<210> SEQ ID NO 10
<211> LENGTH: 21
<212> TYPE: RNA
<213> ORGANISM: Artificial Sequence
<220> FEATURE:
<223> OTHER INFORMATION: non-targeting siRNA antisense strand

<400> SEQUENCE: 10 uugauuguu uagucgcuau u                                               21
```